United States Patent
Shokri

(10) Patent No.: US 12,329,623 B2
(45) Date of Patent: Jun. 17, 2025

(54) ARTIFICIAL URETHRAL SPHINCTER

(71) Applicant: BIOMAGTEC, INC., Dover, DE (US)

(72) Inventor: Pourya Shokri, Tehran (IR)

(*) Notice: Subject to any disclaimer, the term of this patent is extended or adjusted under 35 U.S.C. 154(b) by 1078 days.

(21) Appl. No.: 17/181,108

(22) Filed: Feb. 22, 2021

(65) Prior Publication Data

US 2021/0177566 A1   Jun. 17, 2021

Related U.S. Application Data

(60) Provisional application No. 62/980,155, filed on Feb. 22, 2020.

(51) Int. Cl.
*A61F 2/00* (2006.01)

(52) U.S. Cl.
CPC ...... *A61F 2/0018* (2013.01); *A61F 2210/009* (2013.01); *A61F 2220/0033* (2013.01); *A61F 2230/0069* (2013.01); *A61F 2250/0007* (2013.01)

(58) Field of Classification Search
CPC .............. A61F 2/0018; A61F 2210/009; A61F 2220/0033; A61F 2230/0069; A61F 2250/0007; A61F 2250/0001; A61F 2250/0004; A61F 2250/001; A61F 2/0036; A61F 2/00; A61F 2/0004; A61F 2/0009; A61F 2/0031; A61F 2/0045
See application file for complete search history.

(56) References Cited

U.S. PATENT DOCUMENTS

| | | | |
|---|---|---|---|
| 6,074,341 A | 6/2000 | Anderson et al. | |
| 6,409,656 B1 | 6/2002 | Sangouard et al. | |
| 9,717,579 B2* | 8/2017 | Clement | A61M 60/88 |
| 2003/0225311 A1* | 12/2003 | Sayet | A61F 2/004 |
| | | | 600/29 |

(Continued)

FOREIGN PATENT DOCUMENTS

| | | | | |
|---|---|---|---|---|
| CN | 102821702 A | * | 12/2012 | A61F 2/2445 |
| EP | 1586283 A2 | * | 10/2005 | A61F 2/0036 |

(Continued)

OTHER PUBLICATIONS

Extended European Search Report for European Application No. 21926414.0 dated Jan. 9, 2025.

(Continued)

*Primary Examiner* — Alex M Valvis
*Assistant Examiner* — Julie Thi Tran
(74) *Attorney, Agent, or Firm* — Potomac Law Group, PLLC; Reza Sadr

(57) ABSTRACT

An artificial urethral sphincter. The artificial urethral sphincter includes a cuff member, a hollow cylinder, a spring, and a cable. The cuff member includes a first layer and a second layer, which define an internal pocket between the first layer and the second layer. The cuff member is configured to encircle a urethra of a patient when the cuff member is wrapped around the urethra of the patient. The hollow cylinder is configured to be disposed inside the patient's body. The spring is disposed inside the hollow cylinder. A first part of the cable is disposed inside the internal pocket.

(Continued)

100

The first part of the cable is configured to block the urethra of the patient through gripping the urethra of the patient when the first part of the cable is pulled out of the internal pocket.

35 Claims, 24 Drawing Sheets

(56) References Cited

U.S. PATENT DOCUMENTS

| | | | |
|---|---|---|---|
| 2009/0062825 A1* | 3/2009 | Pool | A61F 5/0066 |
| | | | 606/157 |
| 2011/0071558 A1* | 3/2011 | Dlugos, Jr. | A61F 5/0059 |
| | | | 606/157 |
| 2012/0184980 A1* | 7/2012 | Anderson | A61F 2/0036 |
| | | | 606/192 |
| 2016/0074196 A1* | 3/2016 | Forsell | A61F 5/0059 |
| | | | 128/831 |
| 2017/0065402 A1* | 3/2017 | Tozzi | A61M 60/148 |

FOREIGN PATENT DOCUMENTS

| | | | |
|---|---|---|---|
| EP | 1284691 B1 | | 12/2006 |
| JP | 2010017540 A | * | 1/2010 |
| WO | WO-2019106563 A1 | * | 6/2019 |

OTHER PUBLICATIONS

International Search Report and Written Opinion, PCT/IB2021/051482, dated Jul. 15, 2021, 11 pages.

\* cited by examiner

102

122

100

ARTIFICIAL URETHRAL SPHINCTER

CROSS-REFERENCE TO RELATED APPLICATION

This application claims the benefit of priority from U.S. Provisional Patent Application Ser. No. 62/980,155, filed on Feb. 22, 2020, and entitled "ARTIFICIAL MAGNETIC URETHRAL SPHINCTER" which is incorporated herein by reference in its entirety.

TECHNICAL FIELD

The present disclosure generally relates to medical implants, and particularly relates to an artificial sphincter and, more particularly, to an artificial urethral sphincter.

BACKGROUND

Urinary incontinence is generally defined as the involuntary leakage of urine. In simple terms, urinary incontinence is to urinate when not intended to. In other words, urinary incontinence is the inability to hold urine in the bladder became voluntary control over the urinary sphincter is either lost or weakened. Urinary inconsistence is a much more common problem than most people think. For example, In the United Kingdom, it is estimated that at least three million people, that is approximately equal to 5% of the total population of the United Kingdom, suffer from urinary incontinence. The US Department of Health and Human Services estimates that approximately 13 million Americans suffer from urinary incontinence.

Treatment for urinary incontinence depends on the type of incontinence, the severity of the problem, and also the underlying cause. In most cases, physicians suggest patients to try the least invasive treatments such as behavioral techniques and physical therapy, and then move on to other options only if these techniques fail. Behavioral techniques include bladder training, scheduled toilet trips, and diet management. Physical therapies include pelvic floor muscle exercises and electrical stimulation. Often, medications are used in conjunction with behavioral techniques.

There are also some medical devices available such as urethral inserts that are small tampon-like disposable devices inserted into the urethra and act as a plug to prevent leakage. If other treatments are not working, some surgical procedures may be used to fix problems that cause urinary incontinence. These surgical procedures include sling procedures, bladder neck suspension, and artificial urinary sphincter prostheses.

There are known urinary sphincter prostheses consisting of a toric balloon which tightly hugs the urethra, this balloon may be able to be inflated by utilizing a small syringe made of flexible synthetic material and placed in a man's testicles or a woman's labia majora. An auxiliary reservoir, placed in the viscera and linked by tubes to the syringe and balloon, makes it possible to inflate or deflate the latter using a physiological fluid propulsed by the syringe. This reservoir houses a device making it possible to reverse the direction of flow of the fluid which inflates and deflates the balloon. The surgical installation of this urinary sphincter prosthesis is quite tricky as it is made up of three subassemblies linked to a pipe in which a physiological fluid flows. This urinary sphincter prosthesis may be associated with some drawbacks. For example, this urinary prosthesis is relatively bulky and is insufficiently ergonomic which thereby contributes to the psychological discomfort of the patient. There is also a risk of the physiological fluid leakage for these urinary. Furthermore, the size of the balloon can only be adjusted in notches and inflating it leads to folds which bring about excessive compression points on the urethra which may lead to a local necrosis of the tissues.

This type of urinary sphincter prostheses has been improved by providing a device for controlling the physiological fluid which is controlled by magnetic means outside the human body. However, these sphincter prostheses are complex too because of the various components required and the risks of the physiological fluid leaking persist.

Other artificial urinary sphincters also exist which do not operate with a physiological fluid but by means of a mechanical valve controlled directly by a magnetic field applied outside the human body. A type of these artificial urinary sphincters is comprised of a mechanical clip provided around the duct to be sealed and one of its branches is coupled to a solenoid controlled by an internal energy sensor. This sensor receives waves from a transmitter outside the human body, converts them and transmits them to the solenoid to open the clip. Another type of these artificial urinary sphincters is made up of a mechanical valve, part of which comprises a permanent magnet activated by an electromagnet arranged outside the human body. In both cases, the magnetic control only controls the valve of the artificial sphincter in on-off mode, i.e. only opening or closing it. None of these devices makes it possible to adjust the degree to which this mechanical valve is closed.

There is, therefore, a need for an artificial urinary sphincter which is simple, inexpensive, and ergonomic with minimum discomfort of the patient and minimum risk of malfunction in long-term use.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to an exemplary embodiment, the present disclosure describes an artificial urethral sphincter. In an exemplary embodiment, the disclosed artificial urethral sphincter may include a cuff member, a hollow cylinder, a spring, and a cable. In an exemplary embodiment, the cuff member may include a first layer and a second layer. In an exemplary embodiment, the first layer and the second layer may define an internal pocket between the first layer and the second layer. In an exemplary embodiment, the cuff member may be configured to encircle a urethra of a patient when the cuff member is wrapped around the urethra of the patient and a distal end of the cuff member is attached to a proximal end of the cuff member.

In an exemplary embodiment, the hollow cylinder may be configured to be disposed inside the patient's body. In an exemplary embodiment, the spring may be disposed inside the hollow cylinder. In an exemplary embodiment, a first part of the cable may be disposed inside the internal pocket. In an exemplary embodiment, the first part of the cable may be associated with a first end of the cable. In an exemplary embodiment, the first part of the cable may be connected to a first end of the cable.

In an exemplary embodiment, the first end of the cable may be attached to a distal end of the cuff member. In an exemplary embodiment, the first part of the cable may be configured to block the urethra of the patient through gripping the urethra of the patient when the first part of the cable is pulled out of the internal pocket. In an exemplary embodiment, a second part of the cable may be disposed inside the hollow cylinder. In an exemplary embodiment, the second part of the cable may be associated with a second end of the cable. In an exemplary embodiment, the second end of the cable may be connected to the second part of the cable. In an exemplary embodiment, the second end of the cable may be attached to a second end of the spring. In an exemplary embodiment, a first end of the spring may be attached to a first end of the hollow cylinder.

In an exemplary embodiment, the spring may pull the first part out of the internal pocket through pushing the second end of the spring and the second end of the cable toward a second end of the hollow cylinder. In an exemplary embodiment, the second end of the hollow cylinder may be associated with the second end of the spring. In an exemplary embodiment, the second end of the hollow cylinder may be connected to the second end of the spring.

In an exemplary embodiment, the first part of the cable may be configured to unblock the urethra of the patient by releasing the urethra of the patient when the second end of the spring is pulled toward the first end of the hollow cylinder. In an exemplary embodiment, the artificial urethral sphincter may further include a moveable part attached to the second end of the spring. In an exemplary embodiment, the moveable part may be disposed slidably inside the hollow cylinder.

In an exemplary embodiment, when the moveable part moves inside the hollow cylinder and toward the first end of the hollow cylinder, the second end of the spring may move toward the first end of the hollow cylinder and the first part of the cable may unblock the urethra of the patient through releasing the urethra of the patient.

In an exemplary embodiment, the moveable part may include a magnetic material. In an exemplary embodiment, the moveable part may be configured to urge the second end of the spring to move inside the hollow cylinder and toward the first end of the hollow cylinder and compress the spring when a magnet moves toward the first end of the hollow cylinder.

In an exemplary embodiment, the artificial urethral sphincter may further include a first cuff adjustment mechanism configured to adjust a maximum gripping force applied to the urethra of the patient from the cuff member. In an exemplary embodiment, the first cuff adjustment mechanism may include an adjustment cable and an adjustment screw. In an exemplary embodiment, a first part of the adjustment cable may be disposed inside the hollow cylinder. In an exemplary embodiment, a first end of the adjustment cable may be attached to the second end of the spring. In an exemplary embodiment, the first end of the adjustment cable may be associated with the first part of the adjustment cable.

In an exemplary embodiment, a second end of the adjustment cable may be attached to the adjustment screw. In an exemplary embodiment, the cable may be configured to pull the first end of the spring toward the second end of the hollow cylinder when the adjustment screw is twisted in a first rotational direction. In an exemplary embodiment, the spring may be configured to urge the first end of the spring to move inside the hollow cylinder and toward the first end of the hollow cylinder when the adjustment screw is twisted in a second rotational direction. In an exemplary embodiment, the first rotational direction may be opposite to the second rotational direction.

In an exemplary embodiment, the artificial urethral sphincter may further include a second cuff adjustment mechanism configured to adjust the maximum gripping force applied to the urethra of the patient from the cuff member. In an exemplary embodiment, the second cuff adjustment mechanism may include an adjustment cylinder, a helical slot, and a cap part.

In an exemplary embodiment, the adjustment cylinder may include a hollow structure. In an exemplary embodiment, the adjustment cylinder may be disposed rotatably around the hollow cylinder. In an exemplary embodiment, the adjustment cylinder may include a longitudinal slot on an inner surface of the adjustment cylinder. In an exemplary embodiment, the helical slot may be provided on an outer surface of the hollow cylinder.

In an exemplary embodiment, the cap part may be disposed slidably and rotatably inside the hollow cylinder. In an exemplary embodiment, the cap part may be disposed onto the moveable part. In an exemplary embodiment, the cap part may include a pin on an outer surface of the cap part. In an exemplary embodiment, the pin may be disposed slidably inside the longitudinal slot and the helical slot. In an exemplary embodiment, the cap part may be configured to limit movements of the moveable part inside the hollow cylinder. In an exemplary embodiment, when the adjustment cylinder rotates around a first axis, the cap pat may move up and down inside the hollow cylinder.

In an exemplary embodiment, the cap part may be configured to move up inside the hollow cylinder when the adjustment cylinder rotates around the first axis and in a first rotational direction. In an exemplary embodiment, the cap part may be configured to move down inside the hollow cylinder when the adjustment cylinder rotates around the first axis in a second rotational direction. In an exemplary embodiment, the first rotational direction may be opposite to the second rotational direction.

In an exemplary embodiment, the second cuff adjustment mechanism may further include a lock mechanism. In an exemplary embodiment, the lock mechanism may include a lock pin, a lock spring, and a plurality of pin receiving holes. In an exemplary embodiment, the lock pin may be disposed slidably inside a lock hole of a base. In an exemplary embodiment, the base may be attached to the hollow cylinder.

In an exemplary embodiment, the lock spring may be disposed between the base and a pin plate. In an exemplary embodiment, the pin plate may be attached to the lock pin. In an exemplary embodiment, the lock spring may be configured to urge the lock pin to move upward inside the lock hole by applying an upward force to the pin plate.

In an exemplary embodiment, the plurality of pin receiving holes may be provided at a bottom end of the adjustment cylinder. In an exemplary embodiment, each of the plurality of pin receiving holes may be configured to receive the lock pin. In an exemplary embodiment, the lock pin may be configured to prevent rotational movement of the adjustment cylinder around the rotation axis when the lock pin is inserted into a pin receiving hole from the plurality of pin receiving holes. In an exemplary embodiment, the lock spring may be disposed around the lock pin.

In an exemplary embodiment, the lock pin may include a handle attached to the pin plate. In an exemplary embodiment, when the handle is pulled down in a first direction, the lock pin may disengage from the adjustment cylinder. In an exemplary embodiment, when the handle releases, the lock spring may push up the lock pin inside the lock hole.

In an exemplary embodiment, the artificial urethral sphincter may further include an electromotor, and a pull cable. In an exemplary embodiment, the electromotor may be disposed under the hollow cylinder. In an exemplary embodiment, the pull cable may be interconnected between the electromotor and the moveable part. In an exemplary embodiment, the electromotor may be configured to pull the second end of the spring toward the first end of the spring utilizing the pull cable when the electromotor rotates in a first rotational direction. In an exemplary embodiment, the electromotor may further be configured to release the second end of the spring when the electromotor rotates in a second rotational direction.

In an exemplary embodiment, the artificial urethral sphincter may further include a solenoid in connection with the electromotor. In an exemplary embodiment, the solenoid may be configured to provide an induction current for the electromotor. In an exemplary embodiment, when the magnet moves toward the solenoid, the electromotor may rotate in the first rotational direction.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
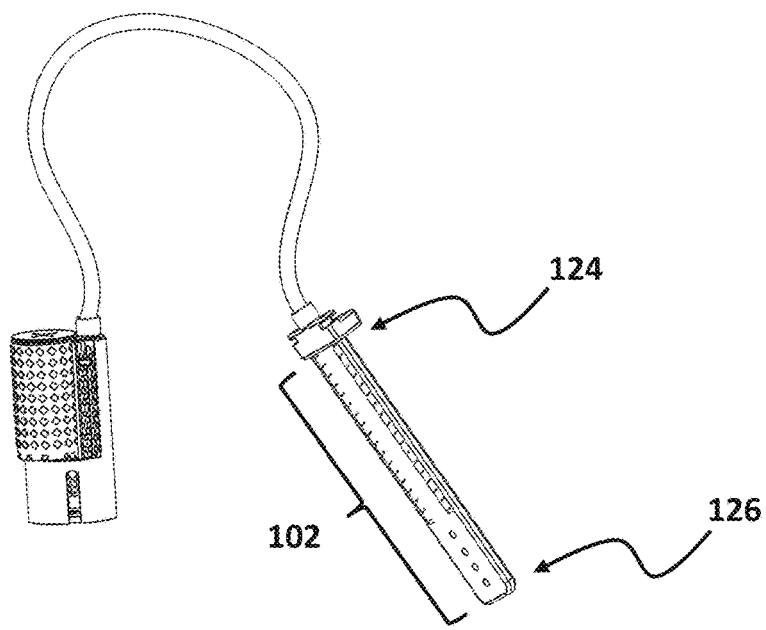
FIG. 1A illustrates an exemplary artificial urethral sphincter, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an artificial urethral sphincter. An exemplary artificial urethral sphincter may include a cuff member, a hollow cylinder, a spring, and a cable. The cuff member may be wrapped around a urethra of a patient and a distal end of the cuff member may be attached to a proximal end of the cuff member. A first part of the cable may be disposed inside an internal pocket of the cuff member. A first end of the cable, which may be connected to the first part of the cable, may be attached to the distal end of the cuff member. The second part of the cable may be disposed inside the hollow cylinder. The spring may be disposed inside the hollow cylinder. A second end of the cable, which may be connected to the second part of the cable, may be attached to a top end of the spring.

In an exemplary embodiment, the spring may push up the second end of the cable inside the hollow cylinder and, thereby, pulling out the first part of the cable from the internal pocket and blocking the urethra of the patient. A magnetic part may be attached to the top end of the spring. In an exemplary scenario, when a user intends to urinate, the user may pull down a first end of an exemplary spring by moving a magnet toward a bottom end of the spring. When a user intends to urinate, the user may move a magnet close to the bottom end of the spring in such a way that a distance between the magnet and the bottom end of the spring becomes less than 1 centimeter. By pulling down the first end of the spring, the cable may be loosened and the urethra of the patient may be unblocked. By utilizing such an artificial urethral sphincter, when a urethra of a patient is blocked by the cuff member and an undesired excess force is applied to the bladder of the patient, the applied excess force may urge the cuff member to unblock the urethra of the patient and, to thereby, may prevent any negative consequences of urinary retention in the bladder of the patient. In other words, the disclosed artificial urethral sphincter artificial urethral sphincter may provide a safety facility for a patient.

Figure 1B:
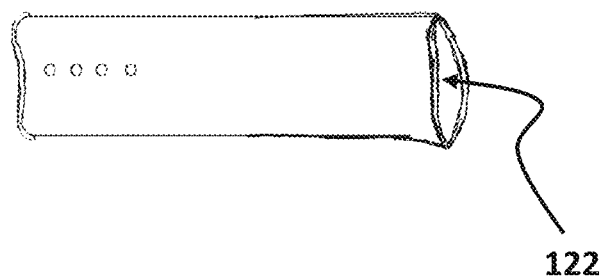
FIG. 1B illustrates a cuff member, consistent with one or more exemplary embodiments of the present disclosure.

FIG. 1A shows an exemplary artificial urethral sphincter 100, consistent with one or more exemplary embodiments of the present disclosure. As shown in FIG. 1A, artificial urethral sphincter 100 may include a cuff member 102. FIG. 1B shows cuff member 102, consistent with one or more exemplary embodiments of the present disclosure. As shown in FIG. 1B, cuff member 102 may include an internal pocket 122.

Figure 1C:
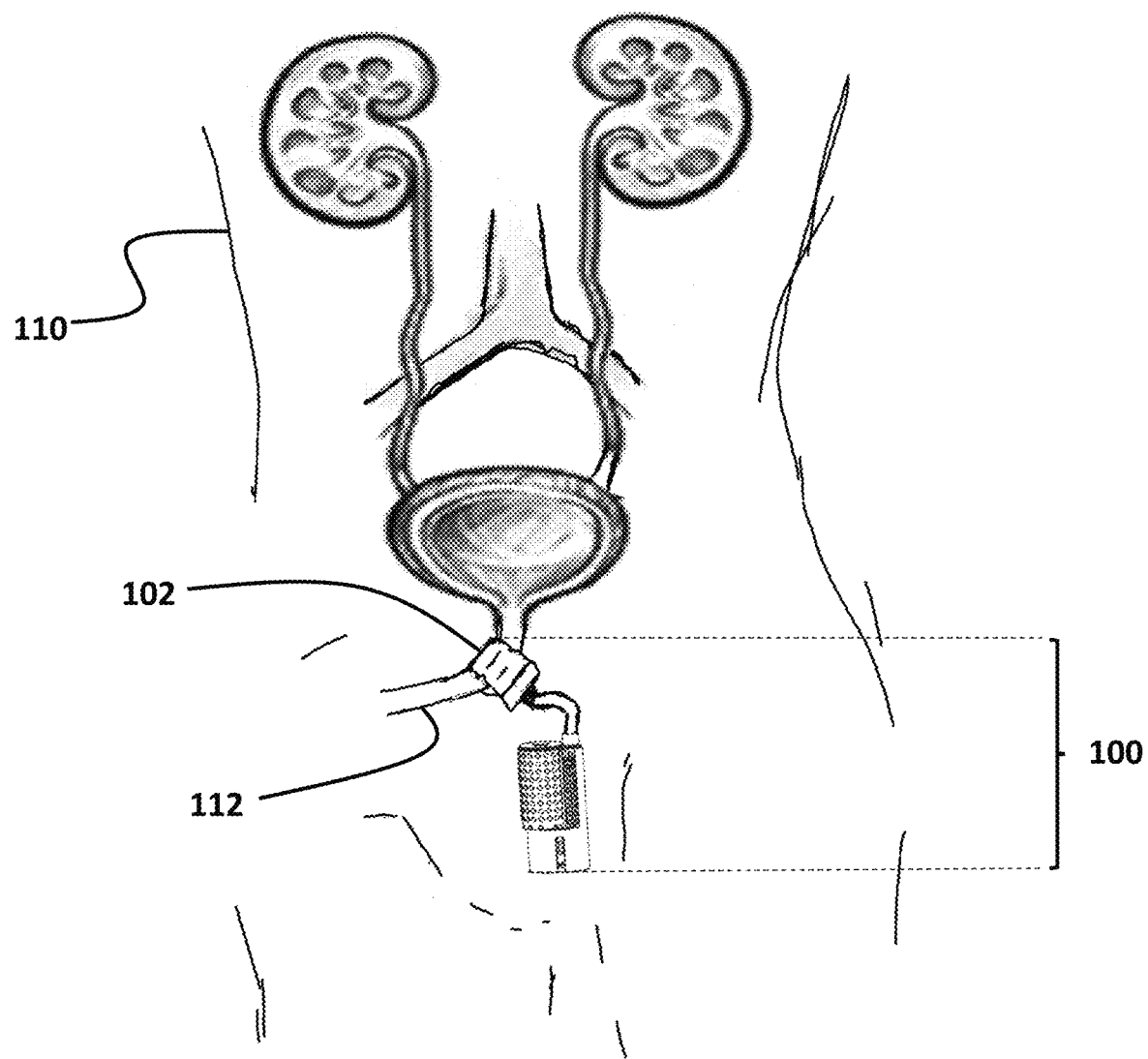
FIG. 1C illustrates an artificial urethral sphincter when the artificial urethral sphincter is implanted inside a patient's body, consistent with one or more exemplary embodiments of the present disclosure.
Figure 1D:
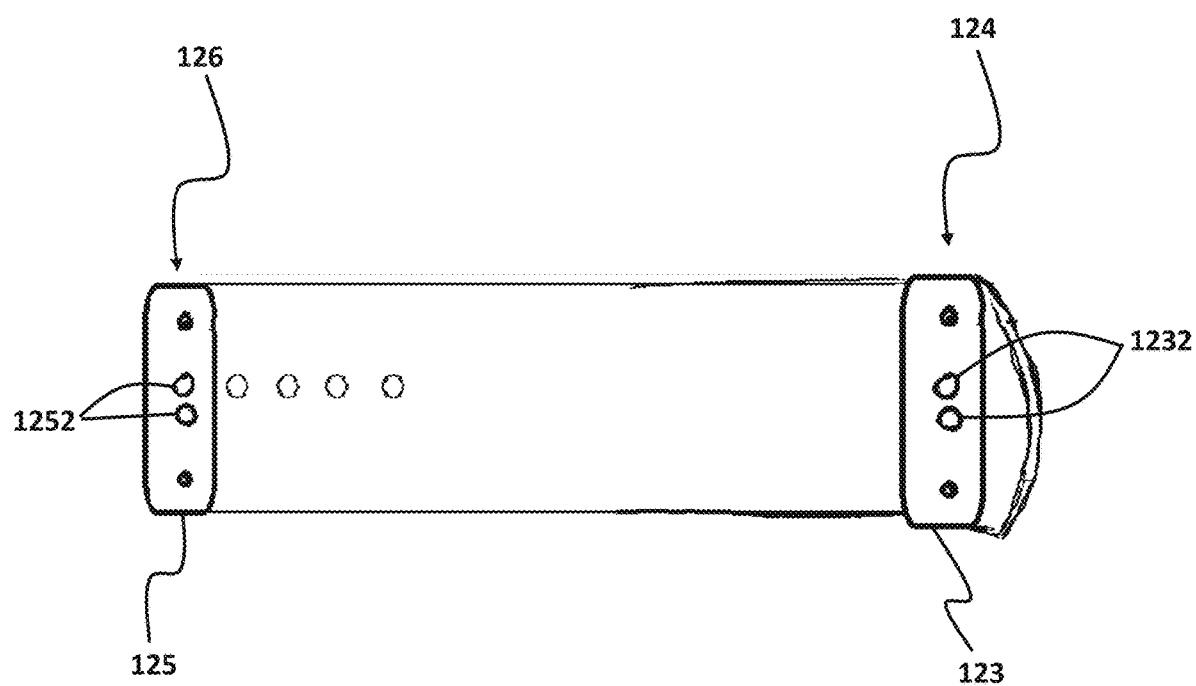
FIG. 1D illustrates an open view of a cuff member, consistent with one or more exemplary embodiments of the present disclosure.

FIG. 1C shows artificial urethral sphincter 100 implanted inside a patient's 110 body, consistent with one or more exemplary embodiments of the present disclosure. As shown in FIG. 1C, cuff member 102 may be configured to encircle a urethra 112 of patient 110. Patient 110 may refer to a person who has a urethra, and is unable to hold urine in the bladder because voluntary control over the urinary sphincter is either lost or weakened. When cuff member 102 encircle urethra 112 of patient 110, cuff member 102 may form a circle around urethra 112 of patient 110. Cuff member 102 may be made up of a flexible material which may allow cuff member 102 to move or deform easily. A user may wrap cuff member 102 around urethra 112 of patient 110. The user may refer to a surgeon. Cuff member 102 may act as a belt around urethra 112 of patient 110. A user may then attach a proximal end 124 of cuff member 102 to a distal end 126 of cuff member 102. FIG. 1D shows an open view of cuff member 102, consistent with one or more exemplary embodiments of the present disclosure.

As shown in FIG. 1D, cuff member 102 may include a first attaching member 123 at proximal end 124 of cuff member 102. Cuff member 102 may further include a second attaching member 125 at distal end 126 of cuff member 102. A user, after wrapping cuff member 102 around urethra 112 of patient 110, may attach first attaching member 123 to second attaching member 125. First attaching member 123 may include a first pair of suture holes 1232. Second attaching member 125 may include a second pair of suture holes 1252. A user, after wrapping cuff member 102 around urethra 112 of patient 110, may attach first attaching member 123 to second attaching member 125 through suturing first attaching member 123 to second attaching member 125 by utilizing first pair of suture holes 1232 and second pair of suture holes 1252.

Figure 2A:
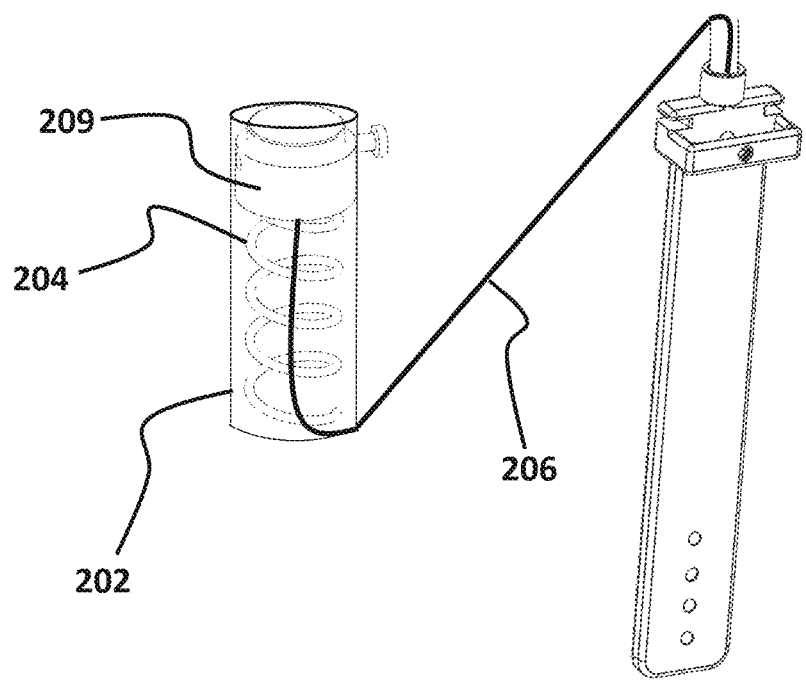
FIG. 2A illustrates an artificial urethral sphincter, consistent with one or more exemplary embodiments of the present disclosure.

FIG. 2A shows artificial urethral sphincter 100, consistent with one or more exemplary embodiments of the present disclosure. As shown in FIG. 2A, artificial urethral sphincter 100 may further include a hollow cylinder 202. Hollow cylinder 202 may be disposed inside patient's 110 body. A user may dispose hollow cylinder 202 inside a perineum (not illustrated) of patient 110. Artificial urethral sphincter 100 may further include a spring 204. Spring 204 may be disposed inside hollow cylinder 202. Spring 204 may be replaced with any elastic object that stores mechanical energy and a length of the object changes when an external force is applied to the object. For example, spring 204 may be replaced with an elastic rubber.

Figure 2B:
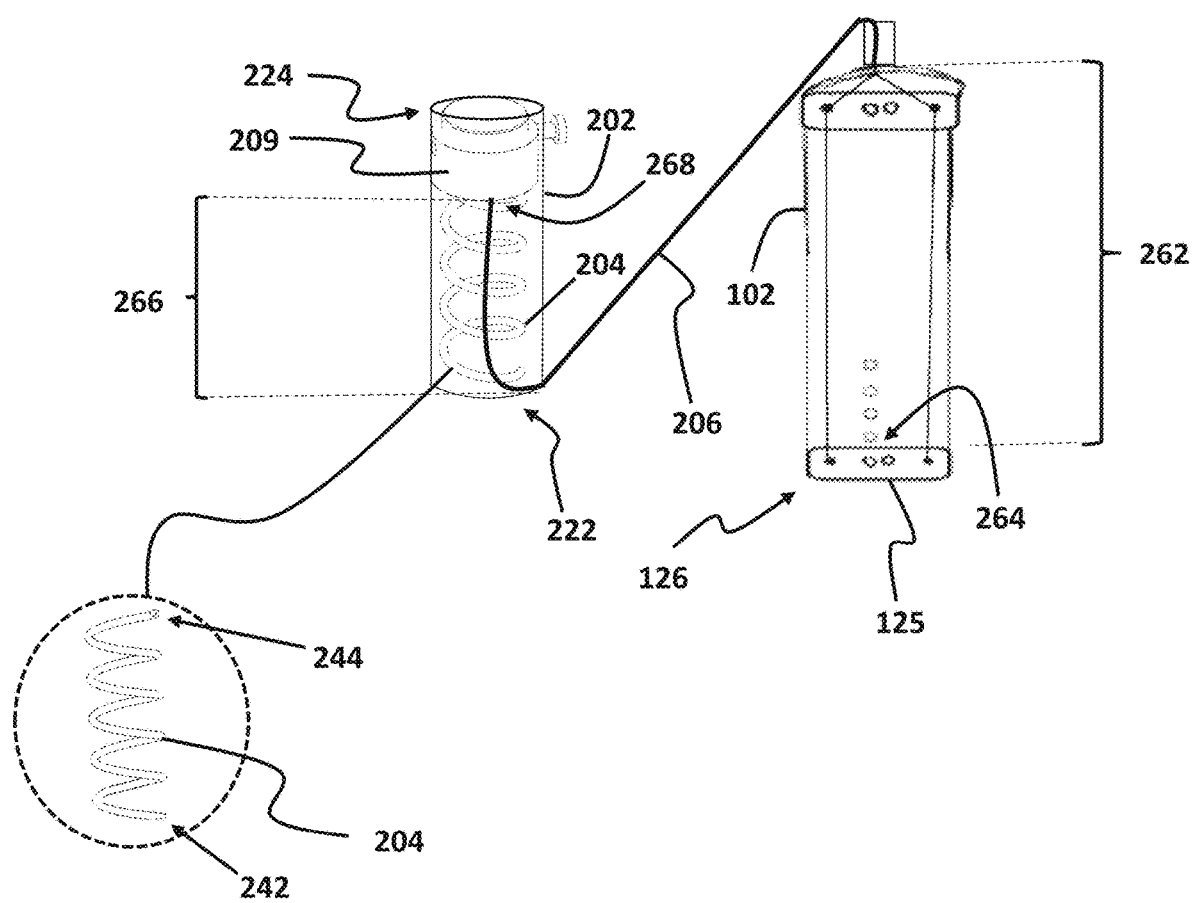
FIG. 2B illustrates an artificial urethral sphincter, consistent with one or more exemplary embodiments of the present disclosure.

FIG. 2B shows artificial urethral sphincter 100, consistent with one or more exemplary embodiments of the present disclosure. As shown in FIG. 2A and FIG. 2B, artificial urethral sphincter 100 may further include a cable 206. A first part 262 of cable 206 may be disposed inside internal pocket 122. A first end 264 of cable 206 may be attached to distal end 126 of cuff member 102. First end 264 of cable 206 may be attached to second attaching member 125. A second part 266 of cable 206 may be disposed inside hollow cylinder 202. Second part 266 of cable 206 may be disposed inside spring 204. Second part 266 of cable 206 may be disposed outside spring 204 and inside hollow cylinder 202. Second end 268 of cable 206 may be attached to a second end 244 of spring 204. Spring 204 may push second end 244 of spring 204 and second end 268 of cable 206 toward a second end 224 of hollow cylinder 202. When spring 204 pushes second end 244 of spring 204 and second end 268 of cable 206 toward second end 224 of hollow cylinder 202, first part 262 of cable 206 may be pulled out of internal pocket 122. When first part 262 of cable 206 is pulled out from internal pocket 122, cuff member 102 may shrink and, thereby, cuff member 102 may grip urethra 112 of patient 110. When cuff member 102 grips urethra 112 of patient 110, urethra 112 of patient 110 may be blocked and, consequently, urine may not be allowed to pass through urethra 112 of patient 110.

Figure 2C:
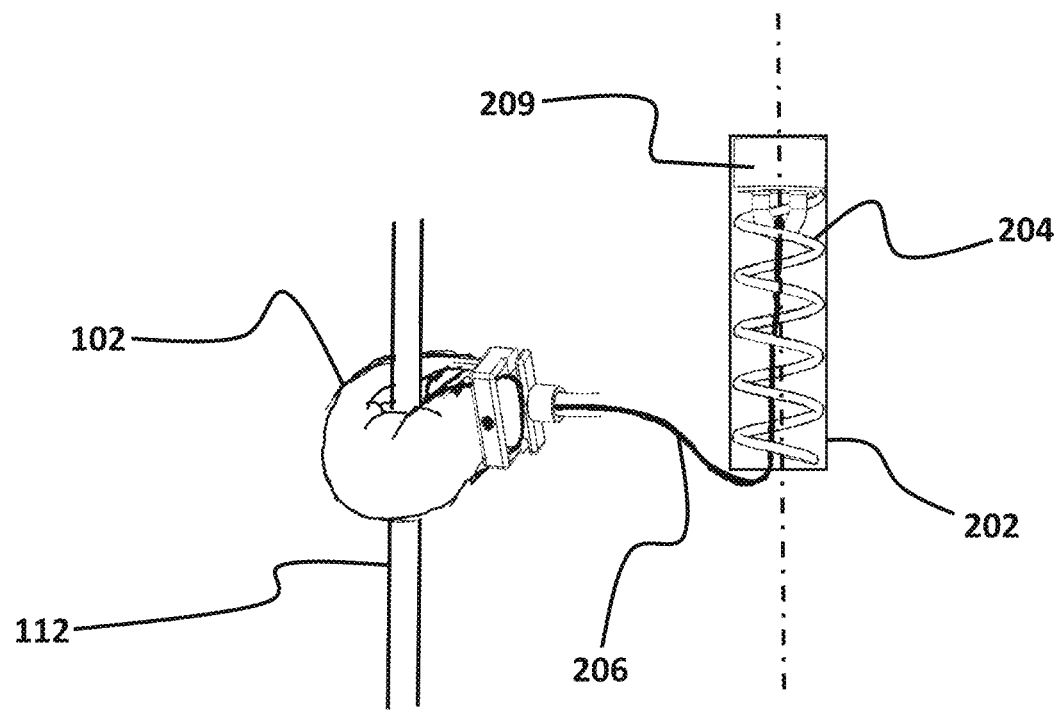
FIG. 2C illustrates an artificial urethral sphincter in a scenario in which a cuff member grips a urethra of a patient and the urethra of the patient is blocked, consistent with one or more exemplary embodiments of the present disclosure.

FIG. 2C shows artificial urethral sphincter 100 in a scenario in which cuff member 102 grips urethra 112 of patient 110 and urethra 112 of patient 110 is blocked, consistent with one or more exemplary embodiments of the present disclosure.

Figure 2D:
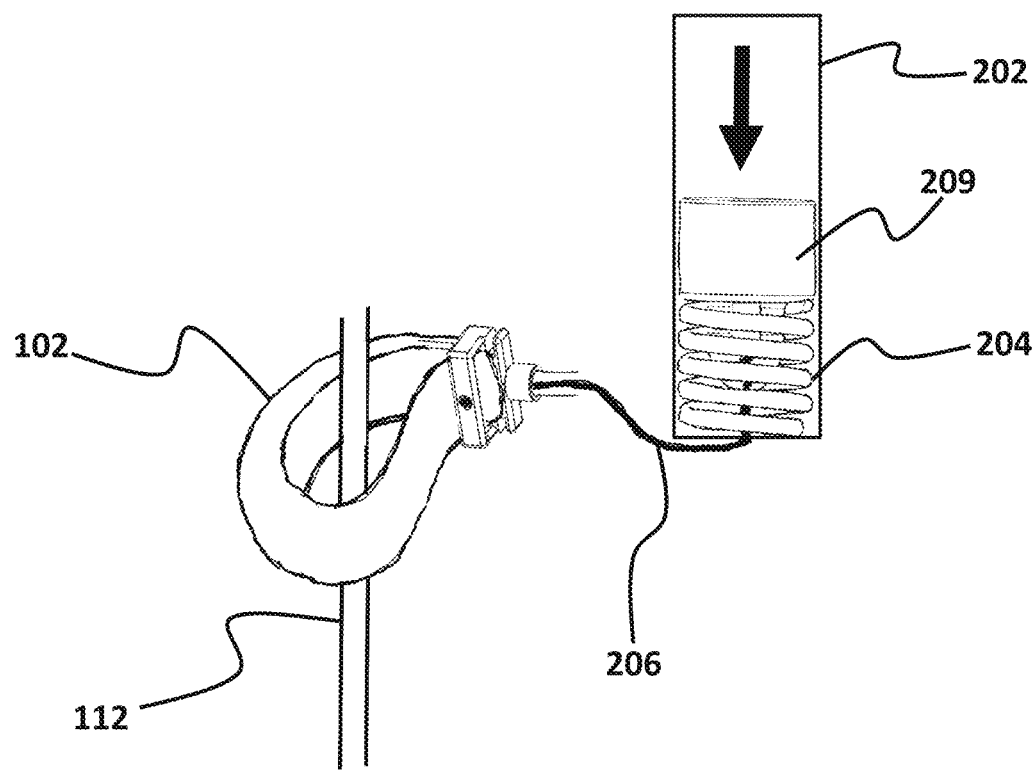
FIG. 2D illustrates an artificial urethral sphincter in a scenario in which a urethra of a patient is released and unblocked, consistent with one or more exemplary embodiments of the present disclosure.

Artificial urethral sphincter 100 may further include a moveable part 209. Moveable part 209 may be disposed slidably inside hollow cylinder 202. Moveable part 209 may include a magnet. Moveable part 209 may be made up of a magnetic material. When moveable part 209 is disposed slidably inside hollow cylinder 202, it may mean that moveable part 209 is disposed inside hollow cylinder 202 in such a way that moveable part 209 is allowed to move linearly inside hollow cylinder 202. Moveable part 209 may be allowed to move linearly along a slide axis 294 inside hollow cylinder 202. Slide axis 294 may coincide a main longitudinal axis of hollow cylinder 202. Moveable part 209 may be attached to second end 244 of spring 204. Moveable part 209 may be disposed onto spring 204. Second end 268 of cable 206 may be attached to a second end 244 of spring 204 through attaching second end 268 of cable 206 to moveable part 209. When moveable part 209 moves toward a first end 222 of hollow cylinder 202, cable 206 may become loose. A cable may become loose when a tensile stress in the cable is zero. In other words, a cable may be loose when no external tensile force is applied to the cable. When cable 206 becomes loose, first part 262 of cable 206 may be loosened accordingly and, thereby, cuff member 102 may release urethra 112 of patient 110. When urethra 112 of patient 110 is released, urethra 112 of patient 110 may be unblocked. When urethra 112 of patient 110 is unblocked, urine may be discharged from bladder and through urethra 112 of patient 110. FIG. 2D shows artificial urethral sphincter 100 in a scenario in which urethra 112 of patient 110 is released and unblocked, consistent with one or more exemplary embodiments of the present disclosure.

Figure 2E:
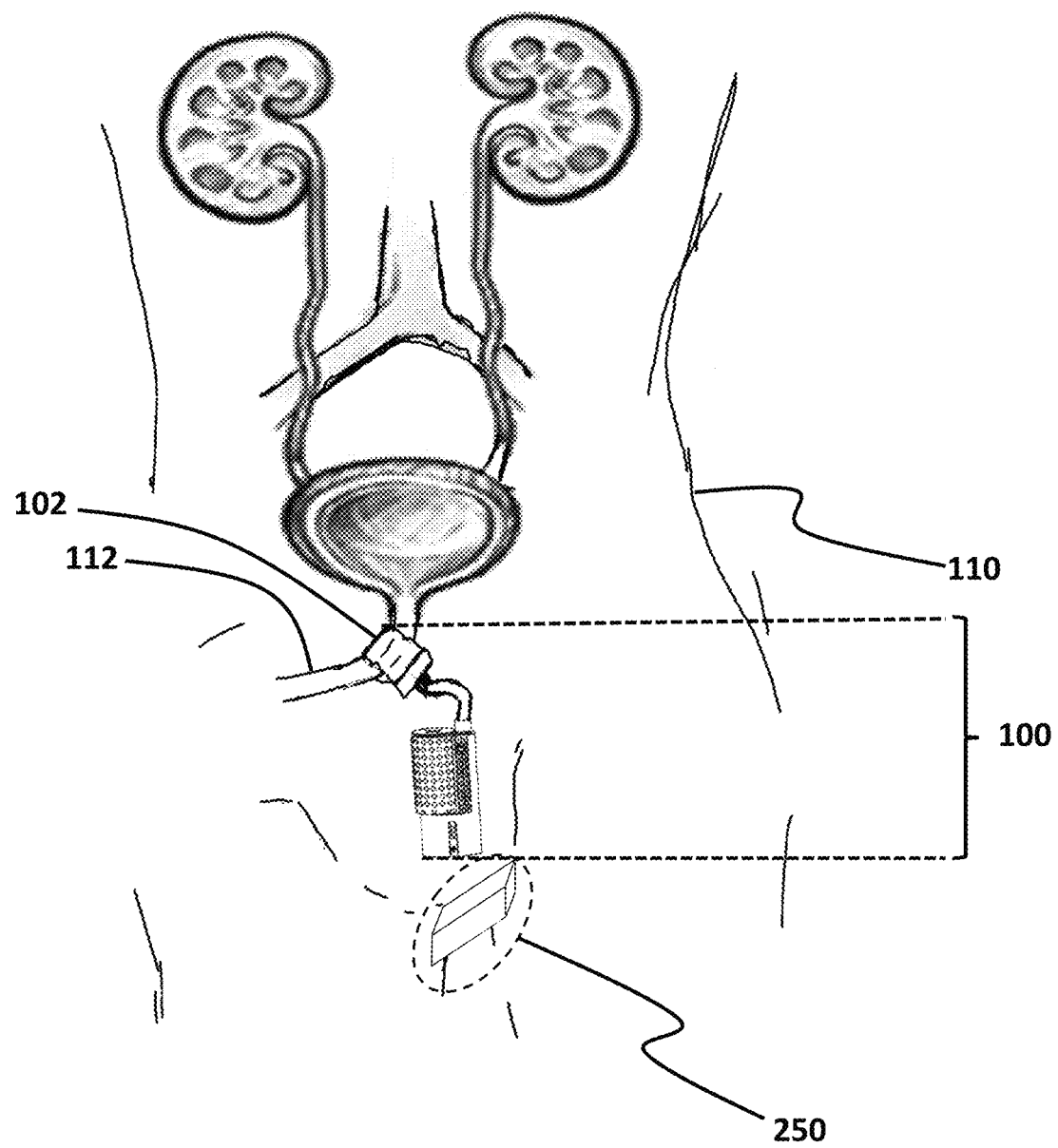
FIG. 2E illustrates an artificial urethral sphincter when the artificial urethral sphincter is implanted inside a patient's body, consistent with one or more exemplary embodiments of the present disclosure.

Moveable part 209 may be made up of a magnetic material. When a part of a magnetic material is disposed inside a magnetic field of a magnet, the part may be urged to move toward the magnet. When a magnet is disposed near to first end 222 of hollow cylinder 202, moveable part 209 may be attracted toward first end 222 of hollow cylinder 202. Patient 110 may unblock urethra 112 of patient 110 by moving a magnet toward first end 222 of hollow cylinder 202. Patient 110 may unblock urethra 112 of patient 110 by moving a magnet close to first end 222 of hollow cylinder 202 in such a way that a distance between the magnet and first end 222 of hollow cylinder 202 becomes less than 1 centimeter. In an absence of an external magnetic field, moveable part 209 may be placed at second end 224 of hollow cylinder 202 and, consequently, urethra 112 of patient 110 may be blocked as discussed above. Then, due to an absence of an external magnetic field, urine may not be allowed to pass through urethra 112 of patient 110. When patient 110 intends to urinate, patient 110 may allow urine discharge from patient's 110 bladder and through urethra 112 of patient 110 by disposing a magnet near to second end 224 of hollow cylinder 202. Cylinder 202 may be disposed inside patient's 110 body in such a way that second end 224 of hollow cylinder 202 is located near to patient's 110 skin so that patient 110 may be able to easily dispose a magnet near to second end 224 of hollow cylinder 202. FIG. 2E shows artificial urethral sphincter 100 when artificial urethral sphincter 100 is implanted inside a patient's 110 body, consistent with one or more exemplary embodiments of the present disclosure. As shown in FIG. 2E, patient 110 may dispose a magnet 250 near to second end 224 of hollow cylinder 202 to unblock urethra 112 of patient 110 and then urine may be discharged from patient's 110 bladder. Magnet 250 may include a magnetic part, a magnetic inductor, an electromagnetic inductor, or a combination thereof.

Figure 3:
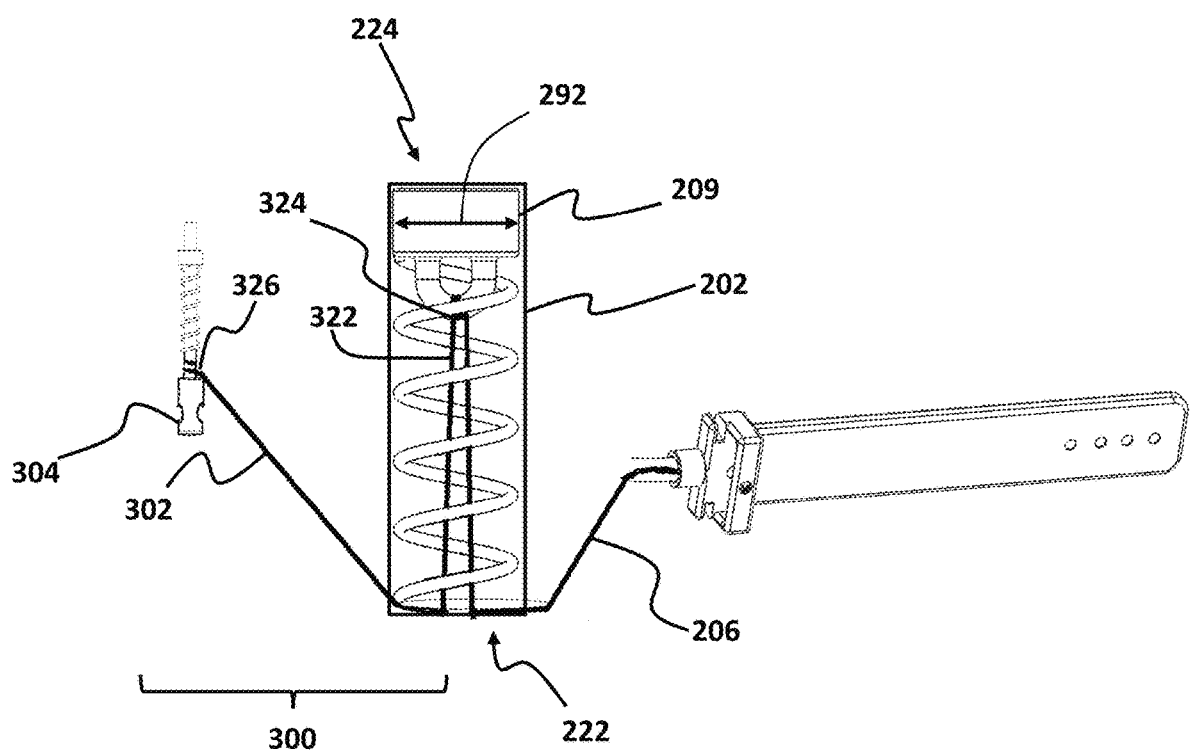
FIG. 3 illustrates an artificial urethral sphincter, consistent with one or more exemplary embodiments of the present disclosure.

FIG. 3 shows artificial urethral sphincter 100, consistent with one or more exemplary embodiments of the present disclosure. As shown in FIG. 3, artificial urethral sphincter 100 may further include a first cuff adjustment mechanism 300. First cuff adjustment mechanism 300 may include an adjustment cable 302. A first part 322 of adjustment cable 302 may be disposed inside hollow cylinder 202. A first end 324 of adjustment cable 302 may be attached to second end 268 of cable 206. First end 324 of adjustment cable 302 may be attached to second end 268 of cable 206 in such a way that adjustment cable 302 and cable 206 create a unitary/integrated cable.

First end 324 of adjustment cable 302 may be attached to second end 244 of spring 204 through attaching first end 324 of adjustment cable 302 to moveable part 209. First part 322 of adjustment cable 302 may be disposed inside spring 204. Spring 204 may be disposed inside hollow cylinder 202.

First cuff adjustment mechanism 300 may further include an adjustment screw 304. A second end 326 of adjustment cable 302 may be attached to adjustment screw 304. A second part of adjustment cable 302 may be wrapped around adjustment screw 304. When adjustment screw 304 is twisted in a first direction, more length of adjustment cable 302 may be wrapped around adjustment screw 304 and, consequently, moveable part 209 may move toward first end 222 of hollow cylinder 202. When moveable part 209 moves toward first end 222 of hollow cylinder 202, cable 206 may be loosened and, consequently, a gripping force that may be applied from cuff member 102 to urethra 112 of patient 110 may decrease. The gripping force may refer to a normal force that may be applied from cuff member 102 to urethra 112 of patient 110 in order to block urethra 112 of patient 110. When adjustment screw 304 is twisted in a second direction, less length of adjustment cable 302 may be maintained wrapped around adjustment screw 304 and, consequently, moveable part 209 may move toward second end 224 of hollow cylinder 202. When moveable part 209 moves toward second end 224 of hollow cylinder 202, cable 206 may be tightened and, consequently, the gripping force that may be applied from cuff member 102 to urethra 112 of patient 110 may increase.

First cuff adjustment mechanism 300 may be used for tightening cable 206. After that artificial urethral sphincter 100 is implanted, first cuff adjustment mechanism 300 may be used to tighten cable 206 so that cable 206 is able to transfer the gripping force appropriately. First cuff adjustment mechanism 300 may allow a same size artificial urethral sphincter 100 to be used for different patients with different urethra sizes. When moveable part 209 is moved down inside hollow cylinder 202, cable 206 may be loosened. First cuff adjustment mechanism 300 may be used to tighten cable 206 and compensate the looseness of cable 206.

First cuff adjustment mechanism 300 may provide significant benefits. For example, a user, for example the surgeon or patient 110 may be able to control the gripping force applied from cuff member 102 to urethra 112 of patient 110 by twisting adjustment screw 304 in the first direction and/or the second direction. For example, the surgeon may be able to increase the gripping force applied from cuff member 102 to urethra 112 of patient 110 by twisting adjustment screw 304 in a clockwise direction and decrease the gripping force applied from cuff member 102 to urethra 112 of patient 110 by twisting adjustment screw 304 in a counterclockwise direction. In instances, without utilizing first cuff adjustment mechanism 300, when magnet 250 is disposed near to second end 224 of hollow cylinder 202, moveable part 209 may be placed at second end 224 of hollow cylinder 202 and, consequently, urethra 112 of patient 110 may be gripped tightly by cuff member 102. On the other hand, in absence of magnet 250, moveable part 209 may be placed at first end 222 of hollow cylinder 202, cuff member 102 may fully release urethra 112 of patient 110 urethra 112 of patient 110. Hence, without utilizing first cuff adjustment mechanism 300, the surgeon or patient 110 may not have a full control on the gripping force applied from cuff member 102 to urethra 112 of patient 110. Adjustment screw 304 may be disposed inside patient's 110 body in such a way that adjustment screw 304 is located near to patient's 110 skin so that a surgeon or patient 110 may be able to easily twist adjustment screw 304 in clockwise or counterclockwise direction.

Extra gripping force may damage urethra 112 of patient 110, that is applying more than a threshold amount of force on urethra 112. The threshold amount of force may be enough so that cuff member 102 grips urethra 112 but does not damage it. Consequently, at first stages of using artificial urethral sphincter 100 for patient 110, adjustment screw 304 may be adjusted in such a way that cuff member 102 applies a relatively low force to urethra 112 of patient 110 so as to minimize a probable damage to urethra 112 of the patient 110. Applying a relatively low force to urethra 112 of patient 110 may refer to applying a pressure between 1000 Pascal and 2500 Pascal to urethra 112 of patient 110. But after using artificial urethral sphincter 100 for a patient for a long time, the previously applied force to urethra 112 of patient 110 may no longer be able to fully grip and block urethra 112 of patient 110. In this scenario, adjustment screw 304 may be twisted in the second direction so as to increase the gripping force applied from cuff member 102 to urethra 112 of patient 110 and, consequently, urine leakage from the urethra 112 of patient 110 may be prevented or otherwise minimized. The gripping force may refer to a normal force that may be applied from cuff member 102 to urethra 112 of patient 110 in order to block urethra 112 of patient 110. After a period of using artificial urethral sphincter 100, urethra 112 of patient 110 may be atrophied and consequently, a size of artificial urethral sphincter 100 may be changed to grip urethra 112 of patient 110 more tightly. In order to change the size of artificial urethral sphincter 100 to grip urethra 112 of patient 110 more tightly, moveable part 209 may be moved down inside hollow cylinder 202 and, thereby, cable 206 may be loosened. In order to tighten first cable 206 and compensate the looseness of cable 206, adjustment screw 304 may be twisted in the second direction so as to increase the gripping force applied from cuff member 102 to urethra 112 of patient 110.

Figure 4A:
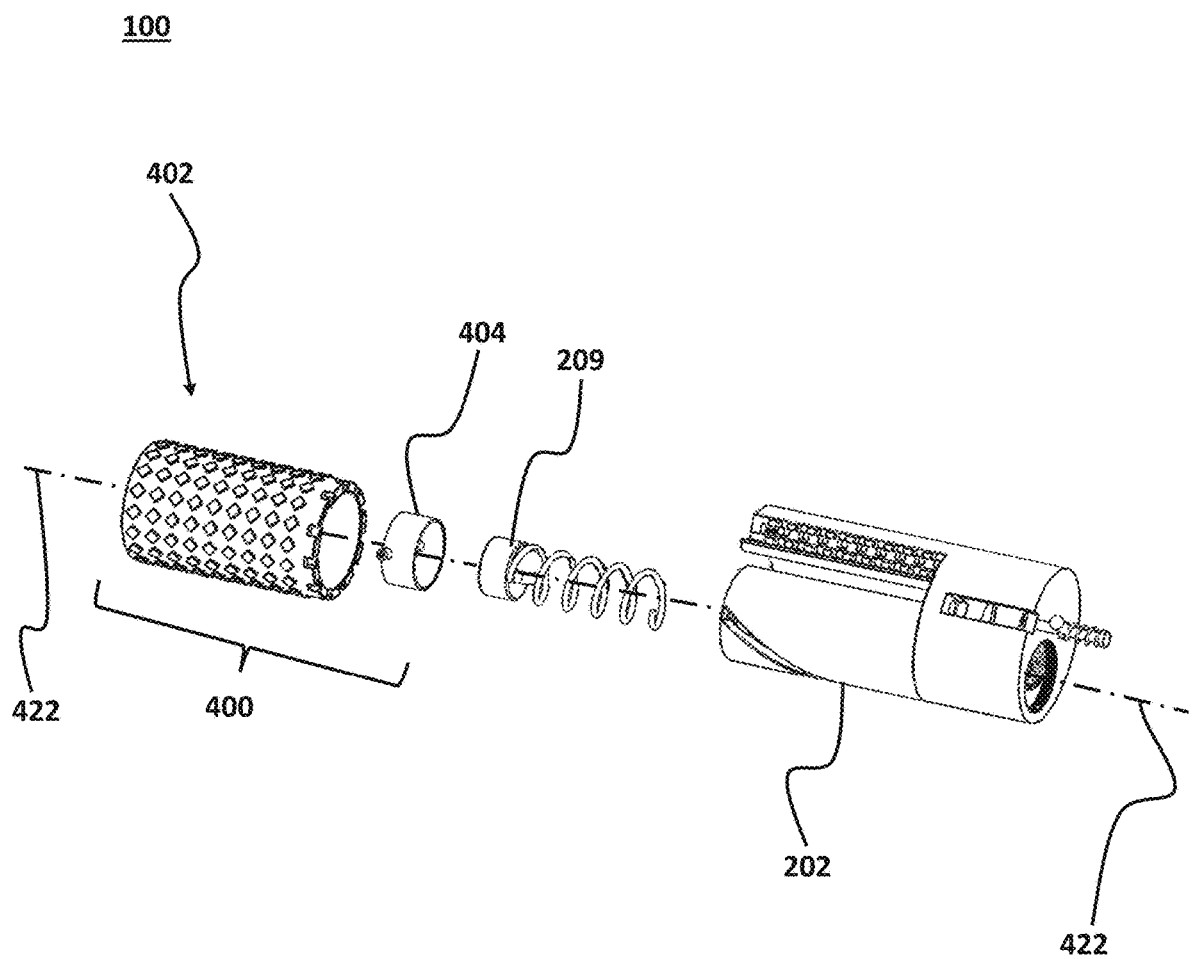
FIG. 4A illustrates an artificial urethral sphincter, consistent with one or more exemplary embodiments of the present disclosure.

FIG. 4A shows artificial urethral sphincter 100, consistent with one or more exemplary embodiments of the present disclosure. As shown in FIG. 4A, artificial urethral sphincter 100 may include a second cuff adjustment mechanism 400. Second cuff adjustment mechanism 400 may be configured to adjust the maximum gripping force applied to urethra 112 of patient 110 from cuff member 102. Second cuff adjustment mechanism 400 may include an adjustment cylinder 402. Adjustment cylinder 402 may be disposed slidably and rotatably around hollow cylinder 202. When adjustment cylinder 402 is disposed rotatably around hollow cylinder 202, it may mean that adjustment cylinder 402 is disposed around hollow cylinder 202 in such a way that adjustment cylinder 402 is able to rotate around an axis such as a rotation axis 422. Rotation axis 422 may be the same as a main axis of hollow cylinder 202 and adjustment cylinder 402. When adjustment cylinder 402 is disposed rotatably around hollow cylinder 202, it may be the same as a scenario in which hollow cylinder 202 is disposed rotatably inside adjustment cylinder 402.

Figure 4B:
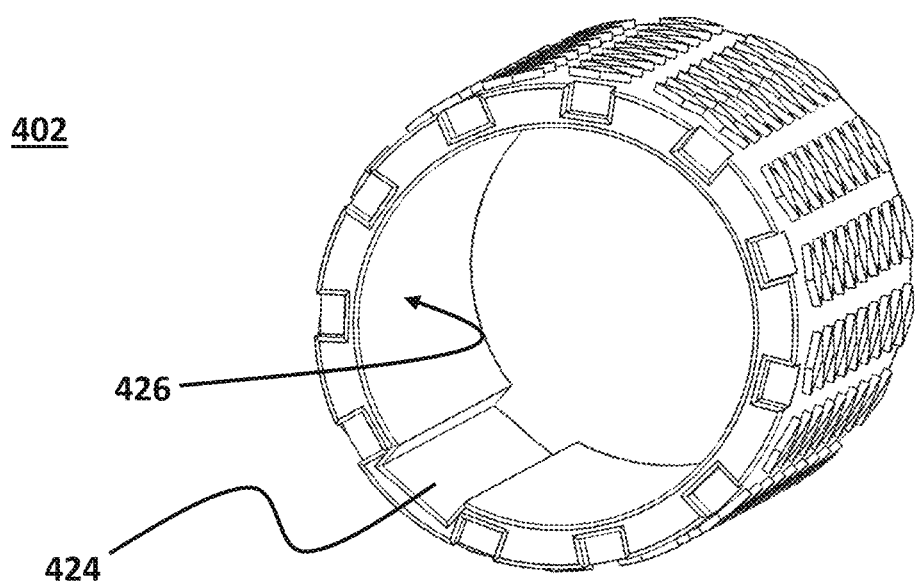
FIG. 4B illustrates a perspective view of an adjustment cylinder, consistent with one or more exemplary embodiments of the present disclosure.

FIG. 4B shows a perspective view of adjustment cylinder 402, consistent with one or more exemplary embodiments of the present disclosure. As shown in FIG. 4B, adjustment cylinder 402 may include a longitudinal slot 424. Longitudinal slot 424 may be provided on an inner surface 426 of adjustment cylinder 402. Longitudinal slot 424 may be provided on inner surface 426 of adjustment cylinder 402 in such a way that a main axis of longitudinal slot 424 is parallel to rotation axis 422.

Figure 4C:
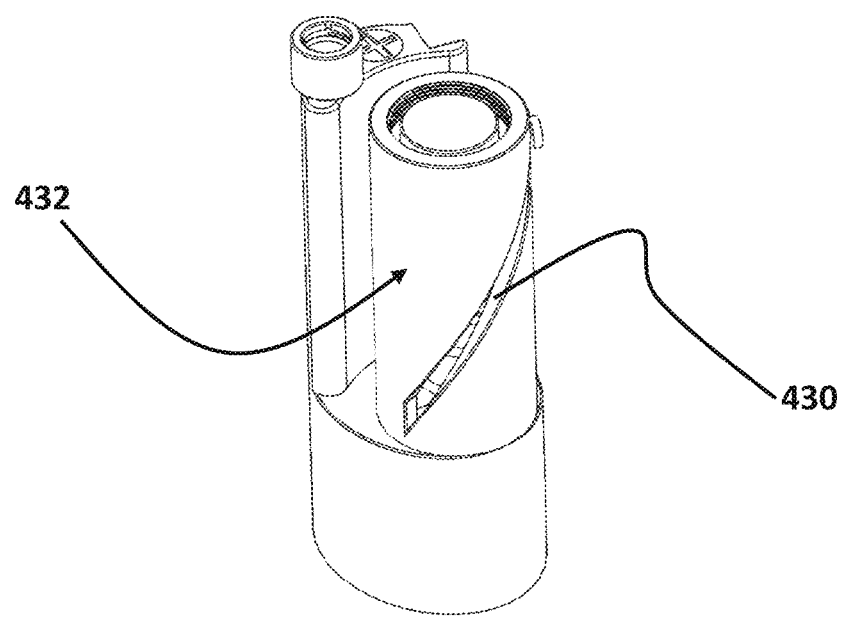
FIG. 4C illustrates a perspective view of a hollow cylinder, consistent with one or more exemplary embodiments of the present disclosure.

FIG. 4C shows a perspective view of hollow cylinder 202, consistent with one or more exemplary embodiments of the present disclosure. Hollow cylinder 202 may include a helical slot 430 on an outer surface 432 of hollow cylinder 202.

Second cuff adjustment mechanism 400 may further include a cap part 404. Cap part 404 may be disposed slidably and rotatably inside hollow cylinder 202. When cap part 404 is disposed slidably and rotatably inside hollow cylinder 202, it may mean that cap part 404 is disposed inside hollow cylinder 202 in such a way that cap part 404 is able to rotate around rotation axis 422 and move linearly along rotation axis 422. Cap part 404 may be disposed onto moveable part 209. In an exemplary scenario when cap part 404 is disposed onto moveable part 209, when cap part 404 moves downward inside hollow cylinder 202, cap part 404 may urge moveable part 209 to move downwardly with moveable part 209 but when cap part 404 moves upward inside hollow cylinder 202, moveable part 209 may not follow cap part 404.

Figure 4D:
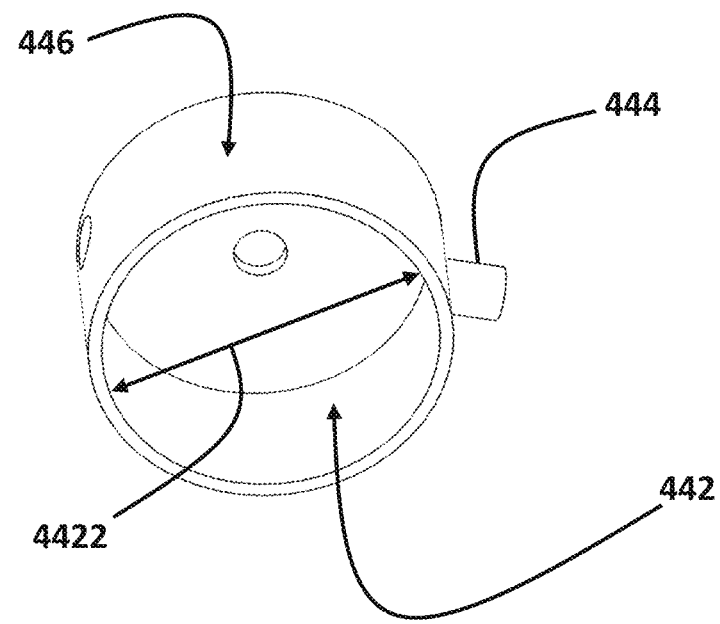
FIG. 4D illustrates a cap part, consistent with one or more exemplary embodiments of the present disclosure.

FIG. 4D shows cap part 404, consistent with one or more exemplary embodiments of the present disclosure. As shown in FIG. 4D, cap part 404 may include an inner chamber 442. Inner chamber 442 may be configured to receive moveable part 209. A diameter 4422 of inner chamber 442 may be slightly larger than an outer diameter 292 of moveable part 209.

Cap part 404 may further include a pin 444 on an outer surface 446 of cap part 404. Pin 444 may be disposed slidably inside longitudinal slot 424 of adjustment cylinder 402. When pin 444 is disposed slidably inside longitudinal slot 424 of adjustment cylinder 402, it may mean that pin 444 may be disposed inside longitudinal slot 424 of adjustment cylinder 402 in such a way that pin 444 is able to move linearly inside longitudinal slot 424 of adjustment cylinder 402. In an exemplary scenario when pin 444 is disposed slidably inside longitudinal slot 424 of adjustment cylinder 402, when cap part 404 moves upward and downward inside hollow cylinder 202, pin 444 may also move upward and downward inside longitudinal slot 424 of adjustment cylinder 402. Moving upward inside hollow cylinder 202 may refer to a movement inside hollow cylinder 202 toward second end 224 of hollow cylinder 202. Moving downward inside hollow cylinder 202 may refer to a movement inside hollow cylinder 202 toward first end 222 of hollow cylinder 202.

Pin 444 may be disposed inside helical slot 430. When pin 444 is disposed inside helical slot 430 and cap part 404 rotates around rotation axis 422, inner surfaces of helical slot 430 may urge pin 444 to move inside helical slot 430. For example, when cap part 404 rotates around rotation axis 422 in a clockwise direction, helical slot 430 may urge pin 444 to move downwardly inside helical slot 430. Then, when cap part 404 rotates around rotation axis 422 in a clockwise direction, cap part 404 may move downwardly inside hollow cylinder 202. Also, when cap part 404 rotates around rotation axis 422 in a counterclockwise direction, helical slot 430 may urge pin 444 to move upwardly inside helical slot 430. Then, it may be understood that when cap part 404 rotates around rotation axis 422 in a counterclockwise direction, cap part 404 may move upwardly inside hollow cylinder 202.

Pin 444 may be disposed inside longitudinal slot 424 and helical slot 430. When adjustment cylinder 402 rotates around rotation axis 422 in a clockwise direction, cap part 404 may rotate around rotation axis 422 synchronously with adjustment cylinder 402 since pin 444 is disposed inside longitudinal slot 424 of adjustment cylinder 402. On the other hand, when cap part 404 rotates around rotation axis 422 in a clockwise direction, cap part 404 may move downward inside hollow cylinder 202. When adjustment cylinder 402 rotates around rotation axis 422 in a counterclockwise direction, cap part 404 may rotate around rotation axis 422 synchronously with adjustment cylinder 402 since pin 444 is disposed inside longitudinal slot 424 of adjustment cylinder 402. On the other hand, when cap part 404 rotates around rotation axis 422 in a counterclockwise direction, cap part 404 may move upward inside hollow cylinder 202.

A surgeon and/or any other user may be able to move cap part 404 downward inside hollow cylinder 202 by rotating adjustment cylinder 402 in a clockwise direction around rotation axis 422. Also, a surgeon and/or any other user may be able to move cap part 404 upward inside hollow cylinder 202 by rotating adjustment cylinder 402 in a counterclockwise direction around rotation axis 422. A surgeon and/or a user may be able to adjust the maximum gripping force that may be applied from cuff member 102 to urethra 112 of patient 110 by rotating adjustment cylinder 402 in a clockwise direction and/or a counterclockwise direction around rotation axis 422. A higher position of cap part 404 inside hollow cylinder 202 may mean that moveable part 209 may be allowed to move upper inside hollow cylinder 202 and, consequently, a greater gripping force may be applied from cuff member 102 to urethra 112 of patient 110. Hence, a user may be able to increase the maximum gripping force that may be applied from cuff member 102 to urethra 112 of patient 110 by rotating adjustment cylinder 402 in a clockwise direction around rotation axis 422.

When adjustment cylinder 402 is rotated in a clockwise direction around rotation axis 422, cap part 404 may move upper inside hollow cylinder 202 which may allow moveable part 209 to move upper inside hollow cylinder 202. When moveable part 209 is able to move upper inside hollow cylinder 202, cuff member 102 may be able to grip urethra 112 of patient 110 more tightly. Also, a surgeon may be able to decrease the maximum gripping force that may be applied from cuff member 102 to urethra 112 of patient 110 by rotating adjustment cylinder 402 in a counterclockwise direction around rotation axis 422. Adjustment cylinder 402 may be located near to patient's 110 skin so that a user may be able to easily rotate adjustment cylinder 402 around rotation axis 422.

Second cuff adjustment mechanism 400 may provide significant benefits. For example, when artificial urethral sphincter 100 is damaged and unable to function appropriately, for example due to a car accident, a surgeon may be able to easily rotate adjustment cylinder 402 around rotation axis 422 in order to unblock urethra 112 of patient 110 and, thereby, the bladder of patient 110 may be discharged.

Figure 5A:
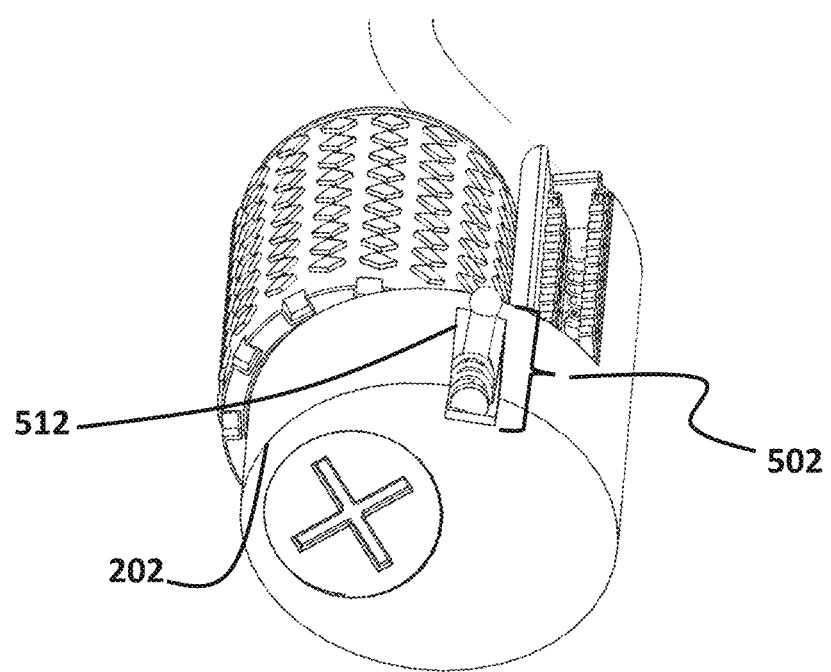
FIG. 5A illustrates a bottom perspective view of an artificial urethral sphincter, consistent with one or more exemplary embodiments of the present disclosure.
Figure 5B:
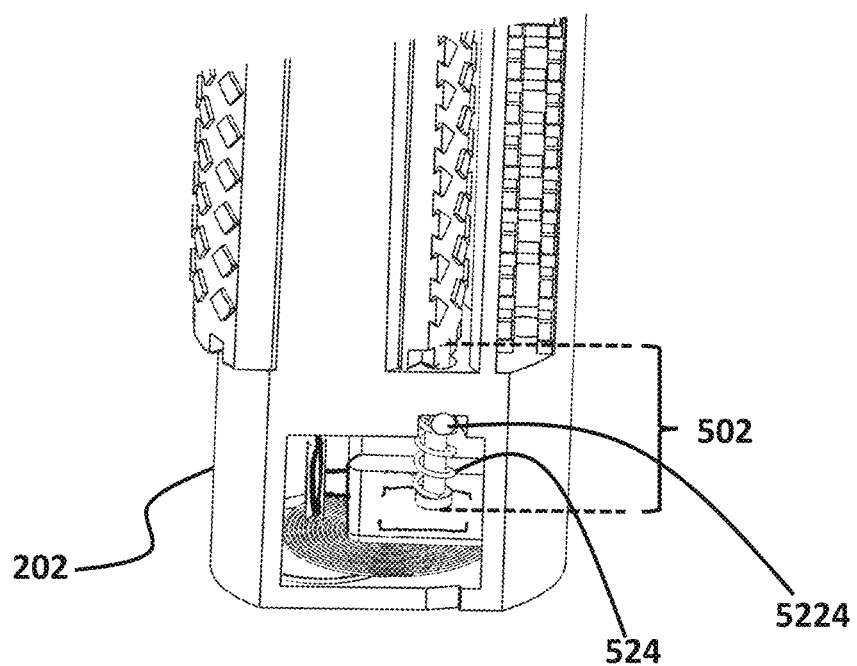
FIG. 5B illustrates a side view of an artificial urethral sphincter, consistent with one or more exemplary embodiments of the present disclosure.

FIG. 5A shows a bottom perspective view of artificial urethral sphincter 100, consistent with one or more exemplary embodiments of the present disclosure. FIG. 5B shows a side view of artificial urethral sphincter 100, consistent with one or more exemplary embodiments of the present disclosure. As shown in FIG. 5A and FIG. 5B, second cuff adjustment mechanism 400 may include a lock mechanism 502.

Figure 5C:
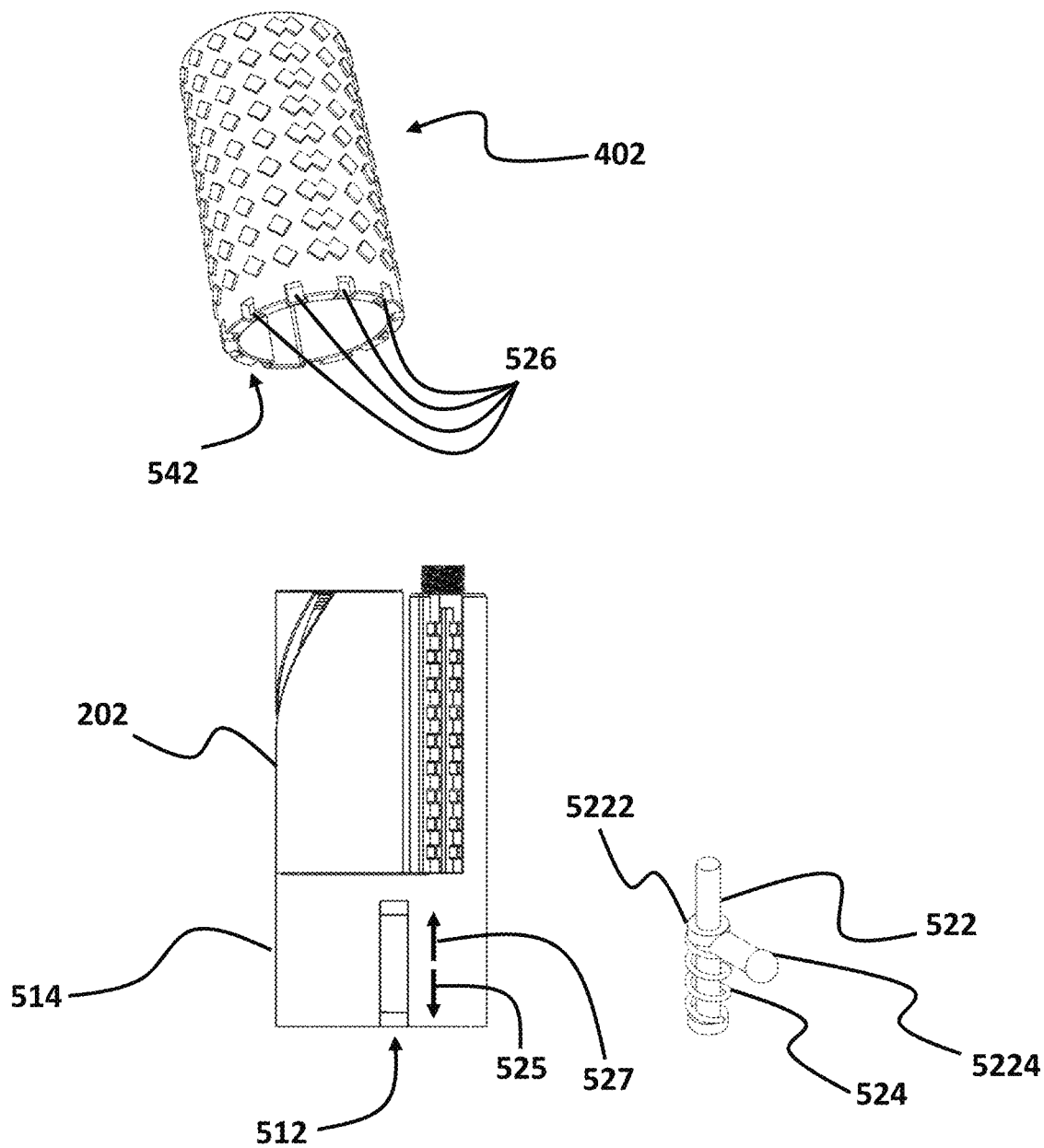
FIG. 5C illustrates an exploded view of an artificial urethral sphincter, consistent with one or more exemplary embodiments of the present disclosure.

FIG. 5C shows an exploded view of artificial urethral sphincter 100, consistent with one or more exemplary embodiments of the present disclosure. As shown in FIG. 5C, lock mechanism 502 may include a lock pin 522, a lock spring 524, and a plurality of pin receiving holes 526. Lock pin 522 may be disposed slidably inside a lock hole 512 of a base 514. Base 514 may be attached to hollow cylinder 202. Base 514 and hollow cylinder 202 may be manufactured seamlessly to create an integrated part. Lock spring 524 may be disposed around lock pin 522. Lock spring 524 may be disposed base 514 and a pin plate 5222. Pin plate 5222 may be attached to lock pin 522. Pin plate 5222 and lock pin 522 may be manufactured seamlessly to create an integrated part. Lock spring 524 may be configured to apply an upward force to pin plate 5222. Lock spring 524 may be configured to urge lock pin 522 to move upward inside lock hole 512 by applying an upward force to pin plate 5222.

As further shown in FIG. 5C, plurality of pin receiving holes 526 may be provided at a bottom end 542 of adjustment cylinder 402. Each of plurality of pin receiving holes 526 may be configured to receive lock pin 522. Lock pin 522 may be configured to prevent or otherwise minimize rotational movement of adjustment cylinder 402 around rotation axis 422 when lock pin 522 is present in a pin receiving hole from plurality of pin receiving holes 526.

Lock pin 522 may include a handle 5224 attached to pin plate 5222. A user may disengage lock pin 522 from adjustment cylinder 402 by pulling down handle 5224 in a first direction 525. When lock pin 522 is pulled down inside lock hole 512 and lock pin 522 is disengaged from adjustment cylinder 402, a user may be able to rotate adjustment cylinder 402 around rotation axis 422. When handle 5224 is released, lock spring 524 may push up lock pin 522 in a second direction 527. When lock pin 522 is pushed up in second direction 527, lock pin 522 may be inserted in a pin receiving hole from plurality of pin receiving holes 526. When lock pin 522 is inserted in a pin receiving hole from plurality of pin receiving holes 526, lock pin 522 may engage with adjustment cylinder 402 and, thereby, rotational movement of adjustment cylinder 402 around rotation axis 422 may be prevented.

FIGS. 6A-6E show artificial urethral sphincter 100, consistent with one or more exemplary embodiments of the present disclosure. As shown in FIGS. 6A-6E, artificial urethral sphincter 100 may further include an electromotor 602 and a solenoid 604. Electromotor 602 may be disposed under hollow cylinder 202. A pull cable 606 may be interconnected between electromotor 602 and moveable part 209. Electromotor 602 may be configured to pull second end 244 of spring 204 toward first end 242 of spring 204 when electromotor 602 rotates in a first rotational direction. Electromotor 602 may further be configured to release second end 244 of spring 204 when electromotor 602 rotates in a second rotational direction. Solenoid 604 may be in connection with electromotor 602. Solenoid 604 may be configured to provide an induction current for electromotor 602. When the magnet 250 moves toward and close to solenoid 604, electromotor 602 may rotate in the first rotational direction and, to thereby, may pull second end 244 of spring 204 toward first end 242 of spring 204. Magnet 250 may include a magnetic part, a magnetic inductor, an electromagnetic inductor, or a combination thereof. When spring 204 has a large spring stiffness constant, electromotor 602 may be used to pull second end 244 of spring 204 toward first end 242 of spring 204.

Figure 6A:
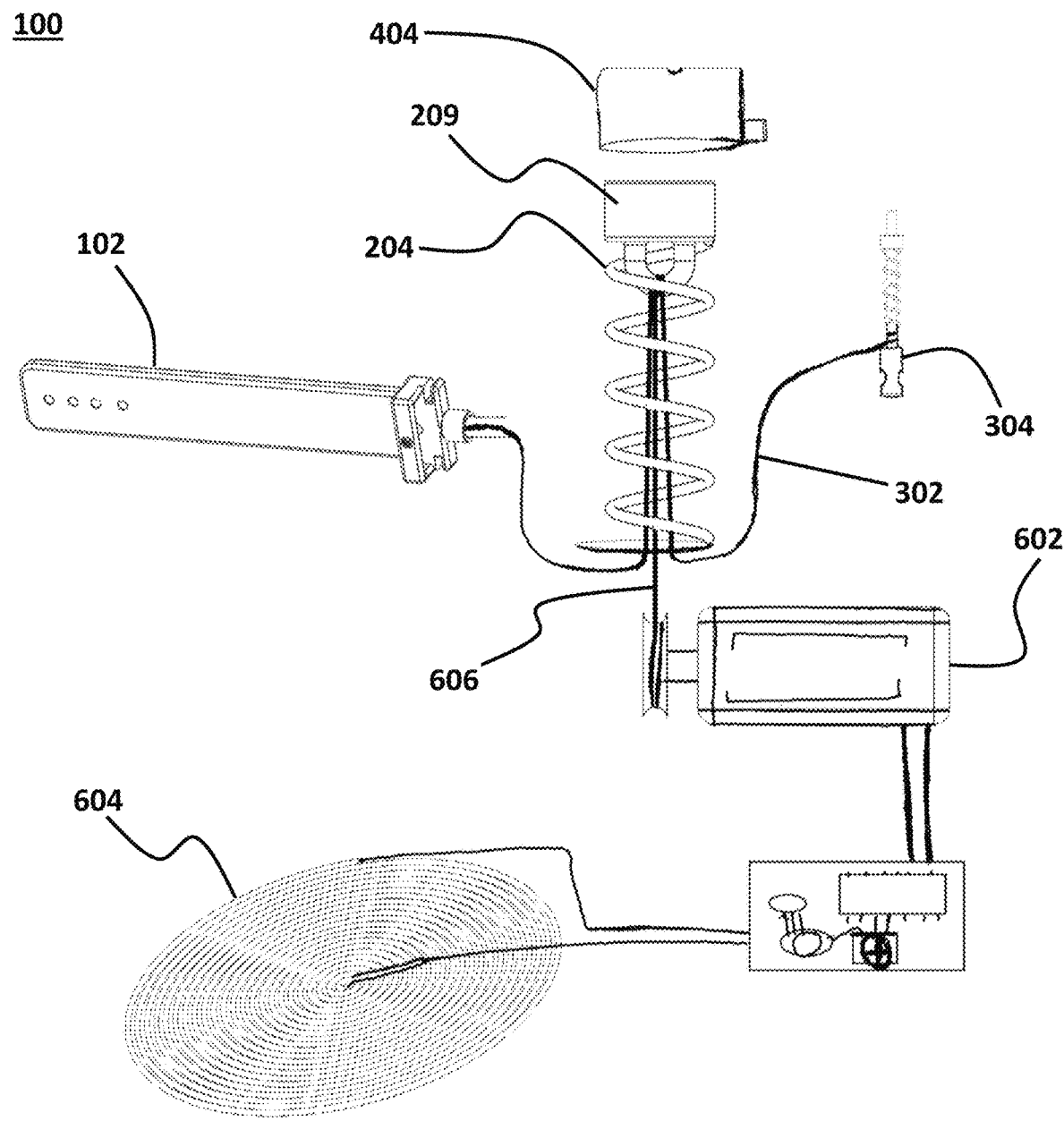
FIG. 6A illustrates an artificial urethral sphincter, consistent with one or more exemplary embodiments of the resent disclosure.
Figure 6B:
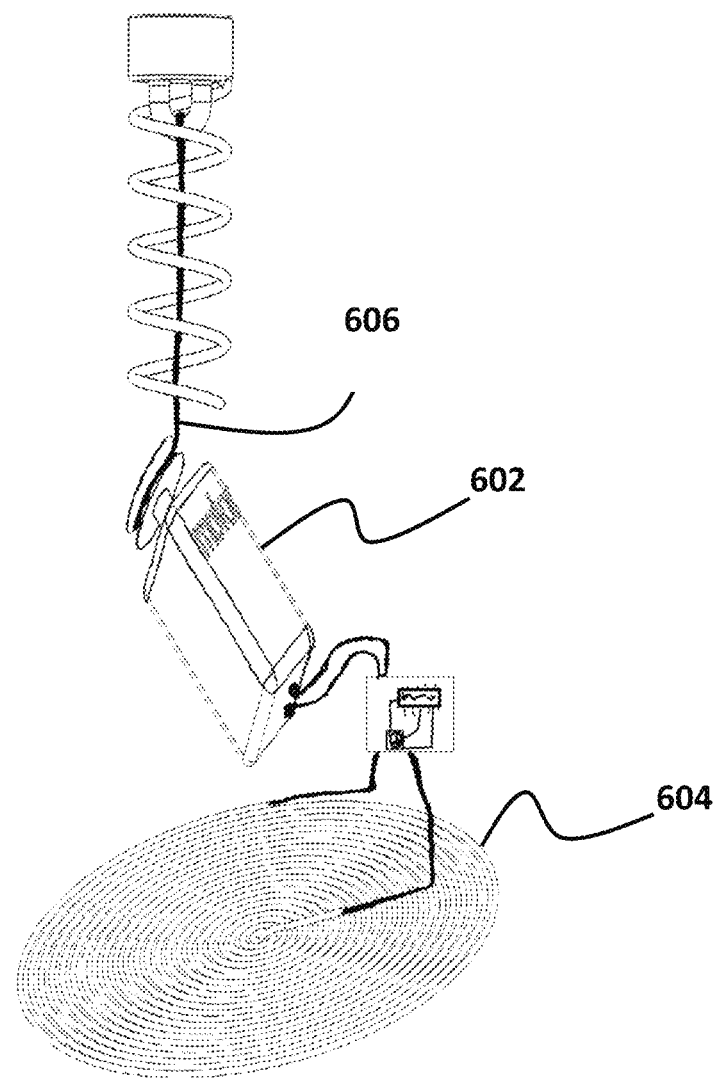
FIG. 6B illustrates an artificial urethral sphincter, consistent with one or more exemplary embodiments of the resent disclosure.
Figure 6C:
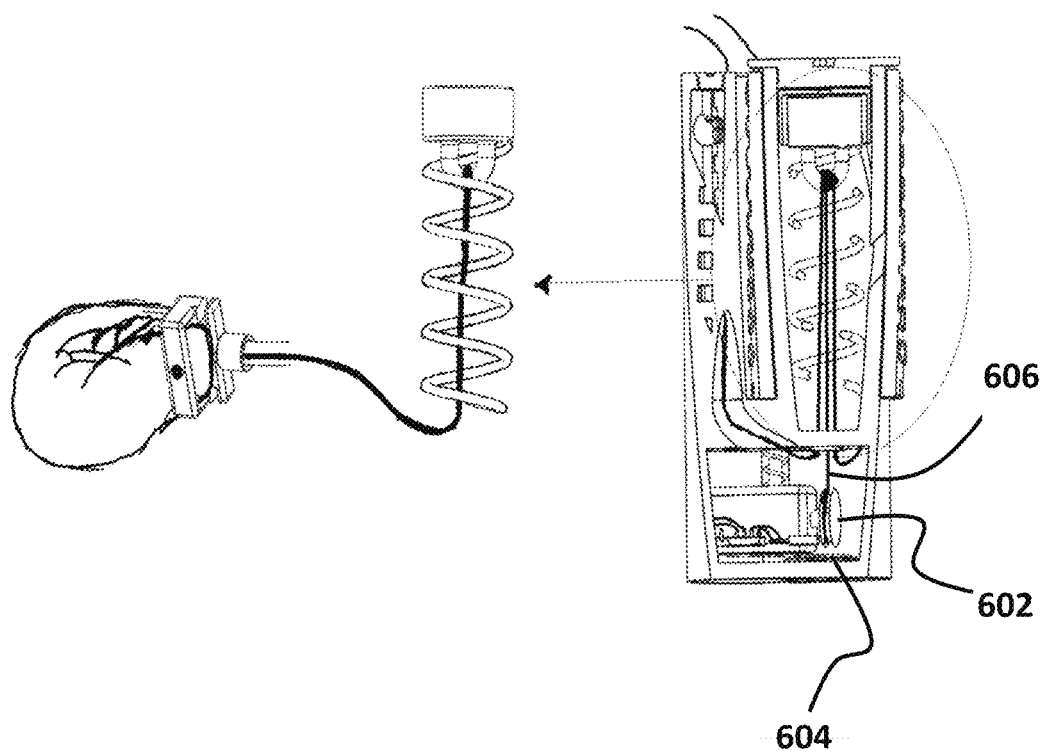
FIG. 6C illustrates an artificial urethral sphincter, consistent with one or more exemplary embodiments of the resent disclosure.
Figure 6D:
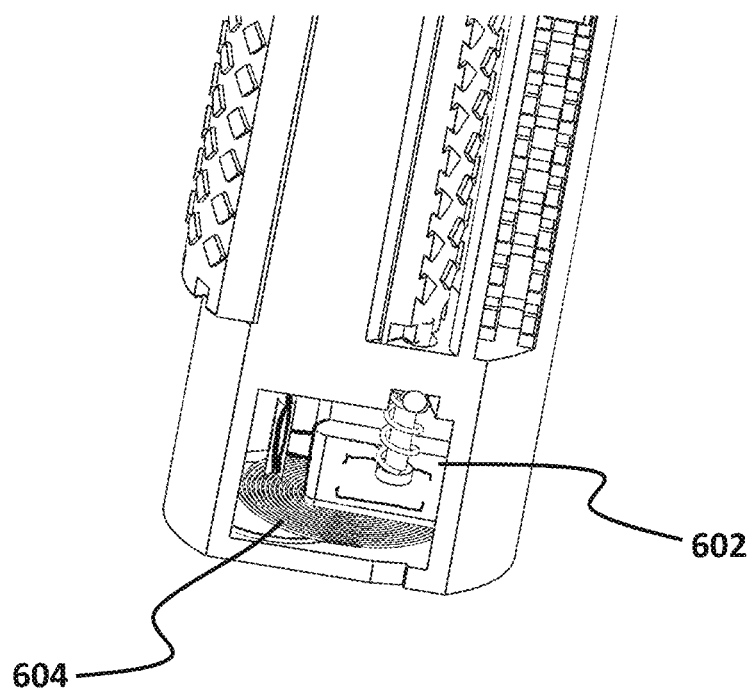
FIG. 6D illustrates an artificial urethral sphincter, consistent with one or more exemplary embodiments of the resent disclosure.
Figure 6E:
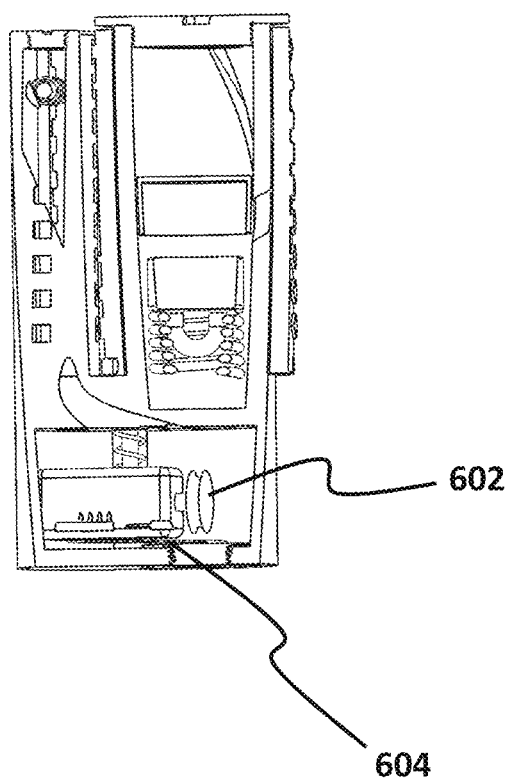
FIG. 6E illustrates an artificial urethral sphincter, consistent with one or more exemplary embodiments of the resent disclosure.
Figure 6F:
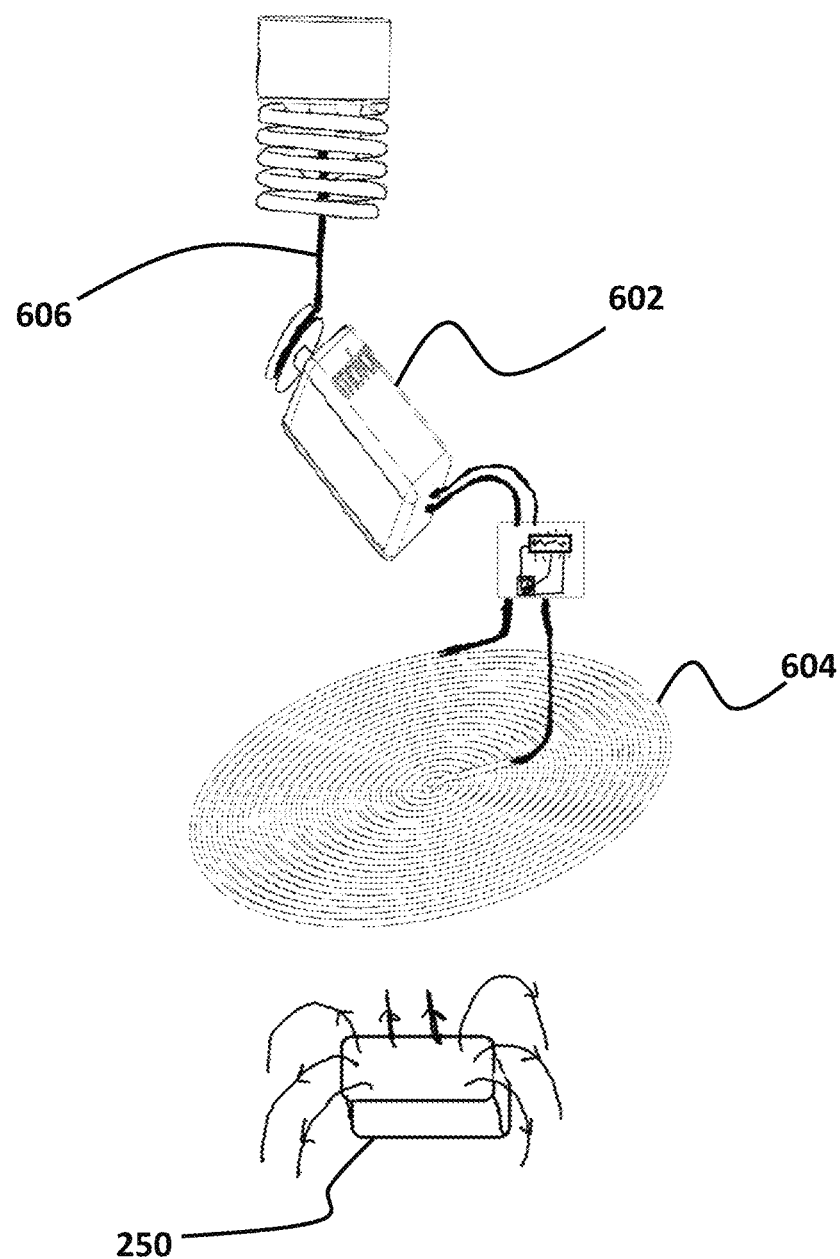
FIG. 6F illustrates an artificial urethral sphincter in a scenario in which a second end of a spring is pulled toward a first end of a spring, consistent with one or more exemplary embodiments of the present disclosure.
Figure 6G:
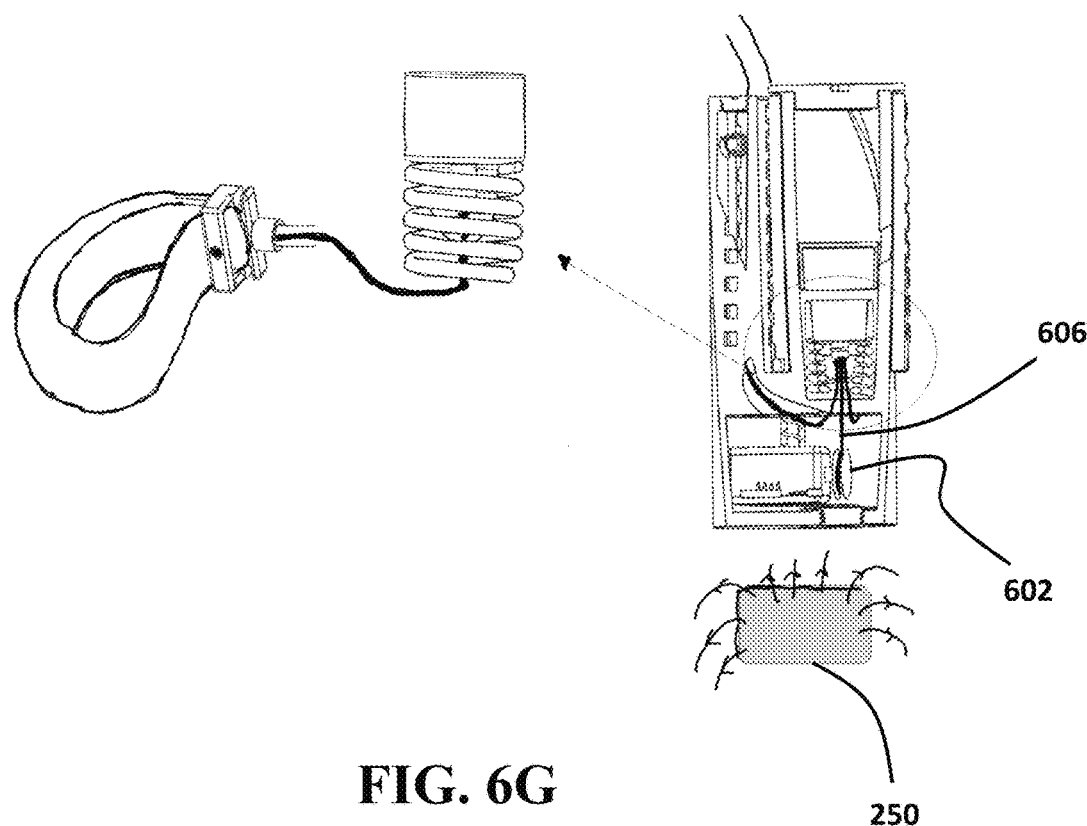
FIG. 6G illustrates an artificial urethral sphincter in a scenario in which a second end of a spring is pulled toward a first end of a spring, consistent with one or more exemplary embodiments of the present disclosure.

FIG. 6F shows artificial urethral sphincter 100 in a scenario in which second end 244 of spring 204 is pulled toward first end 242 of spring 204, consistent with one or more exemplary embodiments of the present disclosure. FIG. 6G shows artificial urethral sphincter 100 in a scenario in which second end 244 of spring 204 is pulled toward first end 242 of spring 204, consistent with one or more exemplary embodiments of the present disclosure.

In an exemplary embodiment, artificial urethral sphincter 100 may further include a controller and a microchip in connection with the electromotor. The controller and the microchip may be configured to control movements of electromotor 602. The controller and the microchip may be in connection with a Bluetooth or wireless module, which may enable the controller and the microchip to be programmed when artificial urethral sphincter 100 is implanted inside patient's 110 body. A size of cuff member 102 and the amount of stretch in cable 206 may be adjusted independently through programming. The controller and the microchip may help artificial urethral sphincter 100 to be developed with artificial intelligence.

In an exemplary embodiment, artificial urethral sphincter 100 may be used as an artificial sphincter for anal sphincter and/or lower esophagus sphincter.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective spaces of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

Moreover, throughout this disclosure, wherever a statement is made to the effect that a feature is present or may be present, it should be understood that the feature is present or may be present in an exemplary embodiment, unless understood otherwise based on the remainder of the disclosure.

The invention claimed is:

1. An artificial sphincter, comprising:
a cuff member configured to encircle a body lumen of a patient;
an electromotor;
an interconnection between the electromotor and the cuff member, the interconnection including a first cable connected to the electromotor and a second cable connected to the cuff member;
a solenoid in connection with the electromotor;
a hollow cylinder; and
a spring disposed inside the hollow cylinder,
wherein:
the solenoid is configured to provide an induction current for the electromotor,
the electromotor is configured to rotate in a first rotational direction or in a second rotational direction in response to the induction current,
the rotation of the electromotor in the first rotational direction causes, through the first cable, a loosening of the second cable and a decrease in a gripping force applied from the cuff member to the body lumen of the patient,
the rotation of the electromotor in the second rotational direction causes, through the first cable, a tightening of the second cable and an increase in the gripping force applied from the cuff member to the body lumen of the patient, the hollow cylinder has a first end and a second end;

the spring has a first end attached to the first end of the hollow cylinder, the spring has a second end attached to the second cable, the interconnection further comprises a moveable part disposed slidably inside the hollow cylinder, the first cable is interconnected between the electromotor and the moveable part, the moveable part is attached to the second end of the spring, and the rotation of the electromotor in the first rotational direction causes, through the first cable, a motion of the moveable part and the second end of the spring inside the hollow cylinder moving toward the first end of the hollow cylinder, causing the loosening of the second cable and the decrease in the gripping force applied from the cuff member to the body lumen of the patient.

2. The artificial sphincter of claim 1, wherein:

the moveable part is further attached to the second cable; and a motion of the moveable part inside the hollow cylinder toward the first end of the hollow cylinder causes the loosening of the second cable and the decrease in the gripping force applied from the cuff member to the body lumen of the patient.

3. The artificial sphincter of claim 2, wherein:

the artificial sphincter further comprises a magnet;

the moveable part comprises a magnetic material; and the moveable part is configured to move inside the hollow cylinder toward the first end of the hollow cylinder responsive to moving the magnet toward the first end of the hollow cylinder, causing the loosening of the second cable and the decrease in the gripping force applied from the cuff member to the body lumen of the patient.

4. An artificial sphincter comprising:

a cuff member configured to encircle a body lumen of a patient;

an electromotor;

an interconnection between the electromotor and the cuff member, the interconnection including a first cable connected to the electromotor and a second cable connected to the cuff member;

a solenoid in connection with the electromotor;

a hollow cylinder;

a spring disposed inside the hollow cylinder; and a cuff adjustment mechanism configured to adjust a maximum gripping force applied to the body lumen of the patient from the cuff member, wherein:

the solenoid is configured to provide an induction current for the electromotor;

the electromotor is configured to rotate in a first rotational direction or in a second rotational direction in response to the induction current;

the rotation of the electromotor in the first rotational direction causes, through the first cable, a loosening of the second cable and a decrease in a gripping force applied from the cuff member to the body lumen of the patient;

the rotation of the electromotor in the second rotational direction causes, through the first cable, a tightening of the second cable and an increase in the gripping force applied from the cuff member to the body lumen of the patient;

the hollow cylinder has a first end and a second end;

the interconnection further comprises a moveable part attached to the second cable;

the moveable part is disposed slidably inside the hollow cylinder;

a motion of the moveable part inside the hollow cylinder moving toward the first end of the hollow cylinder causes the loosening of the second cable and the decrease in the gripping force applied from the cuff member to the body lumen of the patient;

the spring has a first end attached to the first end of the hollow cylinder;

the spring has a second end attached to the second cable; and the cuff adjustment mechanism comprises:

an adjustment cable, a first part of the adjustment cable disposed inside the hollow cylinder, a first end of the adjustment cable attached to the second end of the spring, the first end of the adjustment cable associated with the first part of the adjustment cable; and an adjustment screw, a second end of the adjustment cable attached to the adjustment screw, the adjustment cable configured to pull the second end of the spring toward the first end of the hollow cylinder responsive to twisting the adjustment screw in a first rotational direction, causing a decrease in the maximum gripping force.

5. The artificial sphincter of claim 1, further comprising a magnet, wherein the solenoid is configured to provide the induction current in response to an induction by the magnet.

6. The artificial sphincter of claim 5, wherein the magnet comprises a magnetic part, an electromagnetic inductor, or a combination thereof.

7. The artificial sphincter of claim 5, wherein the solenoid is configured to provide the induction current in response to a movement of the magnet with respect to the solenoid.

8. The artificial sphincter of claim 1, wherein:

the rotation of the electromotor in the second rotational direction causes, through the first cable, a release of the second end of the spring, causing a motion of the second end of the spring moving toward the second end of the hollow cylinder, causing the tightening of the second cable and the increase in the gripping force applied from the cuff member to the body lumen.

9. The artificial sphincter of claim 1, wherein:

the hollow cylinder is configured to be disposed inside the patient's body;

the second cable has a first end and a second end;

the first end of the second cable is attached to the cuff member;

the second end of the spring is attached to the second end of the second cable; and the spring is configured to push the second end of the second cable toward the second end of the hollow cylinder.

10. The artificial sphincter of claim 1, further comprising a cuff adjustment mechanism configured to adjust a maximum gripping force applied to the body lumen from the cuff member.

11. An artificial sphincter, comprising:

a cuff member configured to encircle a body lumen of a patient;

an electromotor;

an interconnection between the electromotor and the cuff member, the interconnection including a first cable connected to the electromotor and a second cable connected to the cuff member;
a solenoid in connection with the electromotor;
a cuff adjustment mechanism configured to adjust a maximum gripping force applied to the body lumen from the cuff member;
a hollow cylinder configured to be disposed inside the patient's body; and
a spring disposed inside the hollow cylinder,
wherein:
  the solenoid is configured to provide an induction current for the electromotor;
  the electromotor is configured to rotate in a first rotational direction or in a second rotational direction in response to the induction current;
  the rotation of the electromotor in the first rotational direction causes, through the first cable, a loosening of the second cable and a decrease in a gripping force applied from the cuff member to the body lumen of the patient;
  the rotation of the electromotor in the second rotational direction causes, through the first cable, a tightening of the second cable and an increase in the gripping force applied from the cuff member to the body lumen of the patient;
  the hollow cylinder has a first end and a second end;
  the second cable has a first end and a second end;
  the first end of the second cable is attached to the cuff member;
  the spring has a first end attached to the first end of the hollow cylinder;
  the spring has a second end attached to the second end of the second cable;
  the spring is configured to push the second end of the second cable toward the second end of the hollow cylinder; and
  the cuff adjustment mechanism is configured to move the second end of the spring toward the first end of the hollow cylinder causing a decrease in the maximum gripping force.

12. The artificial sphincter of claim 11, wherein the cuff adjustment mechanism is further configured to allow the second end of the spring to move toward the second end of the hollow cylinder causing an increase in the maximum gripping force.

13. The artificial sphincter of claim 1, wherein the body lumen is a urethra.

14. The artificial sphincter of claim 1, wherein the artificial sphincter is for an anal sphincter or for a lower esophagus sphincter.

15. The artificial sphincter of claim 1, further comprising a controller in connection with the electromotor and configured to control movements of the electromotor.

16. The artificial sphincter of claim 15, wherein the controller includes a microchip.

17. The artificial sphincter of claim 16, wherein the controller is configured for connection with a wireless module for programming the controller.

18. The artificial sphincter of claim 1, wherein the artificial sphincter is configured to utilize the solenoid to provide the induction current in place of using a battery.

19. An artificial sphincter, comprising:
a cuff member configured to encircle a body lumen of a patient;
an electromotor;
an interconnection between the electromotor and the cuff member, the interconnection including a first cable connected to the electromotor and a second cable connected to the cuff member; and
a solenoid in connection with the electromotor,
wherein:
  the solenoid is configured to provide an induction current for the electromotor,
  the electromotor is configured to rotate in a first rotational direction or in a second rotational direction in response to the induction current;
  the rotation of the electromotor in the first rotational direction causes, through the first cable, a loosening of the second cable and a decrease in a gripping force applied from the cuff member to the body lumen of the patient;
  the rotation of the electromotor in the second rotational direction causes, through the first cable, a tightening of the second cable and an increase in the gripping force applied from the cuff member to the body lumen of the patient;
  the artificial sphincter is configured to be disposed inside the body of the patient; and
  the solenoid is configured to be disposed inside the body of the patient.

20. An artificial sphincter, comprising:
a cuff member configured to encircle a body lumen of a patient;
an electromotor;
an interconnection between the electromotor and the cuff member, the interconnection including a first cable connected to the electromotor and a second cable connected to the cuff member;
a solenoid in connection with the electromotor; and
a magnet,
wherein:
  the solenoid is configured to provide an induction current for the electromotor,
  the electromotor is configured to rotate in a first rotational direction or in a second rotational direction in response to the induction current;
  the rotation of the electromotor in the first rotational direction causes, through the first cable, a loosening of the second cable and a decrease in a gripping force applied from the cuff member to the body lumen of the patient;
  the rotation of the electromotor in the second rotational direction causes, through the first cable, a tightening of the second cable and an increase in the gripping force applied from the cuff member to the body lumen of the patient;
  the solenoid in connection with the electromotor via an electrical connection;
  the solenoid provides the induction current to the electromotor through the electrical connection; and
  the solenoid is configured to provide the induction current in response to an induction by the magnet.

21. The artificial sphincter of claim 20, wherein the electrical connection comprises a controller in electrical connection with the electromotor through a first electrical connection, and a second electrical connection between the solenoid and the controller.

22. The artificial sphincter of claim 20, wherein the magnet comprises a magnetic part, an electromagnetic inductor, or a combination thereof.

23. The artificial sphincter of claim 20, wherein the solenoid is configured to provide the induction current in response to a movement of the magnet with respect to the solenoid.

24. An artificial sphincter, comprising:
a cuff member configured to encircle a bod's y lumen of a patient;
an electromotor;
an interconnection between the electromotor and the cuff member, the interconnection including a first cable connected to the electromotor and a second cable connected to the cuff member;
a hollow cylinder; and
a spring disposed inside the hollow cylinder,
wherein:
the electromotor is configured to rotate in a first rotational direction or in a second rotational direction;
the rotation of the electromotor in the first rotational direction causes, through the first cable, a loosening of the second cable and a decrease in a gripping force applied from the cuff member to the body lumen of the patient;
the rotation of the electromotor in the second rotational direction causes, through the first cable, a tightening of the second cable and an increase in the gripping force applied from the cuff member to the body lumen of the patient;
the hollow cylinder has a first end and a second end;
the spring has a first end attached to the first end of the hollow cylinder;
the spring has a second end attached to the second cable;
the interconnection further comprises a moveable part disposed slidably inside the hollow cylinder;
the first cable is interconnected between the electromotor and the moveable part;
the moveable part is attached to the second end of the spring; and
the rotation of the electromotor in the first rotational direction causes, through the first cable, a motion of the moveable part and the second end of the spring inside the hollow cylinder moving toward the first end of the hollow cylinder, causing the loosening of the second cable and the decrease in the gripping force applied from the cuff member to the body lumen of the patient.

25. The artificial sphincter of claim 24, wherein:
the artificial sphincter further comprises a magnet;
the moveable part comprises a magnetic material; and
the moveable part is configured to move inside the hollow cylinder toward the first end of the hollow cylinder responsive to moving the magnet toward the first end of the hollow cylinder, causing the loosening of the second cable and the decrease in the gripping force applied from the cuff member to the body lumen of the patient.

26. The artificial sphincter of claim 24, wherein the body lumen is a urethra.

27. The artificial sphincter of claim 24, wherein the artificial sphincter is for an anal sphincter or for a lower esophagus sphincter.

28. The artificial sphincter of claim 4, wherein the body lumen is a urethra.

29. The artificial sphincter of claim 4, wherein the artificial sphincter is for an anal sphincter or for a lower esophagus sphincter.

30. The artificial sphincter of claim 11, wherein the body lumen is a urethra.

31. The artificial sphincter of claim 11, wherein the artificial sphincter is for an anal sphincter or for a lower esophagus sphincter.

32. The artificial sphincter of claim 19, wherein the body lumen is a urethra.

33. The artificial sphincter of claim 19, wherein the artificial sphincter is for an anal sphincter or for a lower esophagus sphincter.

34. The artificial sphincter of claim 20, wherein the body lumen is a urethra.

35. The artificial sphincter of claim 20, wherein the artificial sphincter is for an anal sphincter or for a lower esophagus sphincter.

* * * * *